United States Patent
Fogel et al.

(10) Patent No.: US 10,166,207 B2
(45) Date of Patent: *Jan. 1, 2019

(54) ACAMPROSATE FORMULATIONS, METHODS OF USING THE SAME, AND COMBINATIONS COMPRISING THE SAME

(71) Applicant: Synchroneuron Inc., Duxbury, MA (US)

(72) Inventors: Barry S. Fogel, Duxbury, MA (US); William D. Kerns, Duxbury, MA (US); Kei-Lai Fong, Duxbury, MA (US)

(73) Assignee: Synchroneuron, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/421,806

(22) PCT Filed: Jun. 5, 2014

(86) PCT No.: PCT/US2014/041186
§ 371 (c)(1),
(2) Date: Feb. 13, 2015

(87) PCT Pub. No.: WO2014/197744
PCT Pub. Date: Dec. 11, 2014

(65) Prior Publication Data
US 2016/0101075 A1    Apr. 14, 2016

Related U.S. Application Data

(60) Provisional application No. 61/831,587, filed on Jun. 5, 2013.

(51) Int. Cl.
A61K 31/13    (2006.01)
A61K 31/185    (2006.01)
(Continued)

(52) U.S. Cl.
CPC .............. A61K 31/185 (2013.01); A61K 9/20 (2013.01); A61K 9/2027 (2013.01);
(Continued)

(58) Field of Classification Search
CPC .. A61K 31/185; A61K 31/166; A61K 31/517; A61K 9/20; A61K 47/12; A61K 47/32; A61K 45/06
(Continued)

(56) References Cited

U.S. PATENT DOCUMENTS 3,536,809 A    10/1970 Applezweig
3,574,820 A    4/1971 Johnson et al.
(Continued)

FOREIGN PATENT DOCUMENTS

CA    1040533 A1    10/1978
CN    1291091 A    4/2001
(Continued)

OTHER PUBLICATIONS

Guo, Carbopol Polymers Pharmaceutical Drug Delivery Applications, Drug Development & Delivery, vol. 3, No. 6, Sep. 2003, p. 1-4.*
(Continued)

*Primary Examiner* — Taylor V Oh
(74) *Attorney, Agent, or Firm* — Choate, Hall & Stewart LLP; Brenda Herschbach Jarrell

(57) ABSTRACT

Embodiments disclosed herein generally relate to acamprosate formulations, methods of use of the formulations, to methods of using the formulations optionally in combination with at least one other medication, and to combination products and compositions comprising acamprosate and at least one other medication, such as neuroleptic (antipsychotic) and/or antidepressant drugs.

9 Claims, 7 Drawing Sheets

(51) Int. Cl.
*A61K 45/06* (2006.01)
*A61K 47/32* (2006.01)
*A61K 9/20* (2006.01)
*A61K 31/517* (2006.01)
*A61K 47/12* (2006.01)
*A61K 31/166* (2006.01)

(52) U.S. Cl.
CPC .......... *A61K 9/2054* (2013.01); *A61K 9/2072* (2013.01); *A61K 9/2077* (2013.01); *A61K 31/166* (2013.01); *A61K 31/517* (2013.01); *A61K 45/06* (2013.01); *A61K 47/12* (2013.01); *A61K 47/32* (2013.01)

(58) Field of Classification Search
USPC ........................................................ 514/663
See application file for complete search history.

(56) References Cited

U.S. PATENT DOCUMENTS

| | | | |
|---|---|---|---|
| 3,598,123 | A | 8/1971 | Zaffaroni |
| 3,845,770 | A | 11/1974 | Theeuwes et al. |
| 3,901,232 | A | 8/1975 | Michaels et al. |
| 3,916,899 | A | 11/1975 | Theeuwes et al. |
| 3,944,064 | A | 3/1976 | Bashaw et al. |
| 4,008,719 | A | 2/1977 | Theeuwes et al. |
| 4,063,064 | A | 12/1977 | Saunders et al. |
| 4,088,864 | A | 5/1978 | Theeuwes et al. |
| 4,207,890 | A | 6/1980 | Mamajek et al. |
| 4,339,428 | A | 7/1982 | Tencza |
| 4,404,183 | A | 9/1983 | Kawata et al. |
| 4,434,153 | A | 2/1984 | Urquhart et al. |
| 4,536,403 | A | 8/1985 | Rooks |
| 4,690,620 | A | 9/1987 | Simko |
| 4,690,822 | A | 9/1987 | Uemura et al. |
| 4,702,918 | A | 10/1987 | Ushimaru et al. |
| 4,735,804 | A | 4/1988 | Caldwell et al. |
| 4,758,436 | A | 7/1988 | Caldwell et al. |
| 4,767,727 | A | 8/1988 | Claussen et al. |
| 4,851,232 | A | 7/1989 | Urquhart et al. |
| 4,861,598 | A | 8/1989 | Oshlack |
| 4,871,548 | A | 10/1989 | Edgren et al. |
| 4,970,075 | A | 11/1990 | Oshlack |
| 4,992,278 | A | 2/1991 | Khanna |
| 4,996,058 | A | 2/1991 | Sinnreich |
| 5,002,772 | A | 3/1991 | Curatolo et al. |
| 5,007,790 | A | 4/1991 | Shell |
| 5,047,464 | A | 9/1991 | Pogany et al. |
| 5,059,595 | A | 10/1991 | Le Grazie |
| 5,073,543 | A | 12/1991 | Marshall et al. |
| 5,120,548 | A | 6/1992 | McClelland et al. |
| 5,217,712 | A | 6/1993 | Pogany et al. |
| 5,273,758 | A | 12/1993 | Royce |
| 5,354,556 | A | 10/1994 | Sparks et al. |
| RE34,990 | E | 7/1995 | Khanna et al. |
| 5,443,843 | A | 8/1995 | Curatolo et al. |
| 5,458,887 | A | 10/1995 | Chen et al. |
| 5,582,837 | A | 12/1996 | Shell |
| 5,591,767 | A | 1/1997 | Mohr et al. |
| 5,651,985 | A | 7/1997 | Penners et al. |
| 5,674,533 | A | 10/1997 | Santus et al. |
| 5,718,700 | A | 2/1998 | Edgren et al. |
| 5,733,566 | A | 3/1998 | Lewis |
| 5,736,159 | A | 4/1998 | Chen et al. |
| 5,783,212 | A | 7/1998 | Fassihi et al. |
| 5,840,754 | A | 11/1998 | Guittard et al. |
| 5,912,268 | A | 6/1999 | Guittard et al. |
| 5,972,389 | A | 10/1999 | Shell et al. |
| 6,057,373 | A | 5/2000 | Fogel |
| 6,120,803 | A | 9/2000 | Wong et al. |
| 6,294,583 | B1 | 9/2001 | Fogel |
| 6,340,475 | B2 | 1/2002 | Shell et al. |
| 6,365,183 | B1 | 4/2002 | Edgren et al. |
| 6,391,922 | B1 | 5/2002 | Fogel |
| 6,403,120 | B1 | 6/2002 | Sherman et al. |
| 6,426,087 | B1 | 7/2002 | Saslawski et al. |
| 6,451,808 | B1 | 9/2002 | Cowles |
| 6,488,962 | B1 | 12/2002 | Berner et al. |
| 6,514,524 | B1 | 2/2003 | Gryczke |
| 6,548,083 | B1 | 4/2003 | Wong et al. |
| 6,635,280 | B2 | 10/2003 | Shell et al. |
| 6,635,281 | B2 | 10/2003 | Wong et al. |
| 6,682,759 | B2 | 1/2004 | Lim et al. |
| 6,685,962 | B2 | 2/2004 | Friedman et al. |
| 6,689,816 | B2 | 2/2004 | Fogel |
| 6,723,340 | B2 | 4/2004 | Gusler et al. |
| 6,797,283 | B1 | 9/2004 | Edgren et al. |
| 7,405,238 | B2 | 7/2008 | Markey et al. |
| 7,413,751 | B2 | 8/2008 | Devane et al. |
| 7,438,927 | B2 | 10/2008 | Berner et al. |
| 7,498,361 | B2 | 3/2009 | Fogel |
| 7,514,100 | B2 | 4/2009 | Oshlack et al. |
| 7,612,112 | B2 | 11/2009 | Berner et al. |
| 7,731,989 | B2 | 6/2010 | Berner et al. |
| 7,736,667 | B2 | 6/2010 | Berner et al. |
| 7,976,870 | B2 | 7/2011 | Berner et al. |
| 9,421,178 | B2 | 8/2016 | Fogel et al. |
| 9,421,179 | B2 | 8/2016 | Fogel et al. |
| 9,427,420 | B2 | 8/2016 | Fogel et al. |
| 2004/0180088 | A1 | 9/2004 | Dudhara et al. |
| 2005/0249798 | A1 | 11/2005 | Mohammad |
| 2006/0128802 | A1 | 6/2006 | Fogel |
| 2008/0167291 | A1 | 7/2008 | Barlow et al. |
| 2008/0206350 | A1 | 8/2008 | Gryczke |
| 2009/0304753 | A1 | 12/2009 | Tsabari et al. |
| 2009/0304768 | A1 | 12/2009 | Lapidot et al. |
| 2011/0091542 | A1 | 4/2011 | Navon et al. |
| 2011/0195974 | A1 | 8/2011 | Bansal |
| 2011/0244034 | A1 | 10/2011 | Jain et al. |
| 2012/0077878 | A1 | 3/2012 | Berner et al. |
| 2013/0005763 | A1 | 1/2013 | Kanamaru et al. |
| 2013/0143867 | A1 | 6/2013 | Fogel et al. |
| 2013/0224292 | A1 | 8/2013 | Fogel et al. |
| 2013/0245004 | A1 | 9/2013 | Fogel et al. |
| 2013/0310455 | A1 | 11/2013 | Fogel et al. |
| 2013/0310456 | A1 | 11/2013 | Fogel et al. |
| 2015/0119383 | A1 | 4/2015 | Fogel et al. |
| 2015/0250746 | A1 | 9/2015 | Fogel et al. |
| 2016/0081938 | A1 | 3/2016 | Fogel et al. |
| 2017/0042839 | A1 | 2/2017 | Fogel et al. |

FOREIGN PATENT DOCUMENTS

| | | |
|---|---|---|
| CN | 1293573 A | 5/2001 |
| EA | 1382331 A1 | 1/2004 |
| EP | 0661045 A1 | 7/1995 |
| JP | 2002-503686 A | 2/2002 |
| JP | 2002-509104 A | 3/2002 |
| JP | 2010-512317 A | 4/2010 |
| RU | 2284814 C1 | 10/2006 |
| WO | WO-94/27587 A2 | 12/1994 |
| WO | WO-95/19174 A1 | 7/1995 |
| WO | WO-95/29665 A1 | 11/1995 |
| WO | WO-95/30422 A1 | 11/1995 |
| WO | WO-96/00065 A1 | 1/1996 |
| WO | WO-96/08253 A1 | 3/1996 |
| WO | WO-96/13248 A1 | 5/1996 |
| WO | WO-96/25153 A1 | 8/1996 |
| WO | WO-96/26717 A1 | 9/1996 |
| WO | WO-96/26718 A2 | 9/1996 |
| WO | WO-96132097 A1 | 10/1996 |
| WO | WO-96/37202 A1 | 11/1996 |
| WO | WO-96137189 A1 | 11/1996 |
| WO | WO-97/18814 A1 | 5/1997 |
| WO | WO-97/33566 A2 | 9/1997 |
| WO | WO-97/37640 A2 | 10/1997 |
| WO | WO-97/47285 A2 | 12/1997 |
| WO | WO-97/48385 A2 | 12/1997 |
| WO | WO-98/11879 A1 | 3/1998 |
| WO | WO-98/15264 A1 | 4/1998 |
| WO | WO-98/33489 A1 | 8/1998 |
| WO | WO-98/55107 A1 | 12/1998 |
| WO | WO-99/06045 A1 | 2/1999 |

(56) References Cited

FOREIGN PATENT DOCUMENTS

| | | |
|---|---|---|
| WO | WO-99/12527 A2 | 3/1999 |
| WO | WO-99/17745 A1 | 4/1999 |
| WO | WO-99/21551 A1 | 5/1999 |
| WO | WO-99/29297 A1 | 6/1999 |
| WO | WO-99/29305 A1 | 6/1999 |
| WO | WO-99/30692 A1 | 6/1999 |
| WO | WO-99/36064 A2 | 7/1999 |
| WO | WO-99/42086 A1 | 8/1999 |
| WO | WO-03/072087 A1 | 9/2003 |
| WO | WO-2008/073282 A2 | 6/2008 |
| WO | WO-2008/101743 A2 | 8/2008 |
| WO | WO-2011/102506 A1 | 8/2011 |
| WO | WO-2011/143118 A2 | 11/2011 |
| WO | WO-2012/050922 A2 | 4/2012 |
| WO | WO-2013/082573 A1 | 6/2013 |
| WO | WO-2013/085473 A2 | 6/2013 |
| WO | WO-2014/197744 A1 | 12/2014 |

OTHER PUBLICATIONS

U.S. Appl. No. 14/297,388, Fogel et al.
U.S. Appl. No. 61/387,368, Depomed, Inc.
Anilkumar, Gastroretentive drug delivery system: An overview, Pharmainfo.net, 6(1) (2008).
Arzu, et al., Efficacy of low-dose pramipexole augmentation in the treatment of refractory depression complicated with tardive dyskinesia: a case report, Klinik Psikofarmakoloji Bulteni, 21(4).
Baldrick, P., Pharmaceutical excipient development: The need for preclinical guidance, Regulatory Toxicology Pharmaceuticals, 32(2):210-218 (2000).
Burton, S. et al., Intragastric distribution of ion-exchange resins: A drug delivery system for the topical treatment of the gastric mucosa, Pharmacological Pharmaceuticals, 47(11):901-906 (1995).
CAMPRAL® (acamprosate calcium) Delayed-Release Tablets, Highlights of Prescribing Information, 11 pages (2004).
Charman, W.N., Lipids, lipophilic drugs, and oral drug delivery—some emerging concepts, Journal of Pharmacological Science, 89(8):967-978 (2000).
Chawla, G. et al., A Means to Address Regional Variability in Intestinal Drug Absorption, Pharmaceutical Technology, pp. 50-68 (2003).
Dehghan, M.H.G. and Khan, F.N., Gastroretentive Drug Delivery Systems: A Patent Perspective, International Journal of Health Research, 2(1):23-44 (2009).
European Search Report for EP 12853036.7, 5 pages (dated Mar. 25, 2015).
Excipients for Oral Solid Dosage Forms, Lubrizol Life Science Polymers, pp. 1-9 (2013).
Fleisher, D. et al., Drug, Meal and Formulation Interactions Influencing Drug Absorption After Oral Administration, Clin Pharmacokinet, 36(3):233-254 (1999).
Formulating Controlled Release Tablets and Capsules with Carbopol® Polymers, Lubrizol Pharmaceutical Bulletin, 31:pp. 1-22 (2011).
Garg, S. and Sharma, S., Gastroretentive Drug Delivery System, Business Briefing, Pharmatech, 160-166 (2003).
Grant, M. and Baldessarini, R., Possible improvement of neuroleptic-associated tardive dyskinesia during treatment with aripiprazole, the Annals of Pharmacotherapy, 39: p. 1953 (2005).
Guidance for Industry: Food-Effect Bioavailability and Fed Bioequivalence Studies, U.S. Department of Health and Human Services Food and Drug Administration Center for Drug Evaluation and Research (CDER), 12 pages (2002).
Hammarberg, et al., Acamprosate determinations in plasma and cerebrospinal fluid after multiple dosing measured by liquid chromatography—mass spectroscopy: A pharmacokinetic study in healthy volunteers, Therapeutic Drug Monitor, 32:489-496 (2010).
International Search Report for PCT/US12/67507, 5 pages (dated Feb. 13, 2013).
International Search Report for PCT/US2014/041186, 4 pages (dated Sep. 26, 2014).
Kim, S. et al., Effects of $\alpha$1- and $\alpha$2-adrenoreceptor antagonists on cold allodynia in a rat tail model of neuropathic pain, Brain Research, 1039:207-210 (2005).
Lubrizol Corporation, Lubrizol Pharmaceutical Polymers for Controlled Release Tablets and Capsules, Pharmaceutical Bulletin 30:pp. 1-7 (2011).
Lubrizol Corporation, Molecular Weight of Carbopol® and Pemulen™ Polymers, Technical Data Sheet 222:pp. 1-3 (2008).
Merzlikine, A. et al., Effect of chitosan glutamate, carbomer 974P, and EDTA on the in vitro Caco-2 permeability and oral pharmacokinetic profile of acyclovir in rats, Drug Development and Industrial Pharmacy, 35(9):1082-1091 (2009).
Meshali, M. et al., Preparation and Evaluation of Theophylline Sustained-Release Tablets, Drug Development and Industrial Pharmacy, 22(4):373-376 (1996).
Nayak, A.K. et al., Gastroretentive drug delivery systems, a review, Asian Journal of Pharmacetuical and Clinical Research, 3(1):1-10 (2010).
Pinto, João F., Site-specific drug delivery systems within the gastrointestinal tract: From the mouth to the colon, International Journal of Pharmaceutics, 395:44-52 (2010).
PRNewsWire, StarCap1500® co-processed starch excipient receives pharmaceutical precedence of use in the European Union, Electronic Resource: [http://www.prnewswire.com/news-releases/starcap-1500-co-processed-starch-excipient-receives-pharmaceutical-precedence-of-use-in-the-european-union-149484765.html]. Retrieved on Oct. 23, 2014.
Saivin, et al., Clinical pharmacokinetics of acamprosate, Clinical Pharmacokinetics, 35(5):331-345 (1998).
Singh, B. et al., Formulation and optimization of controlled release mucoadhesive tablets of atenolol using response surface methodology, AAPS PharmSciTech., 7(1) Article 3: E19-E28 (2006).
STRIANT® (testosterone buccal system mucoadhesive) package insert, 16 pages (2003).
Sun, C. C. et al., Development of a High Drug Load Tablet Formulation Based on Assessment of Powder Manufacturability: Moving Towards Quality by Design, Journal of Pharmaceutical Sciences, 98:239-247 (2009).
Sungthongjeen et al., Design and evaluation of floating multi-layer coated tablets based on gas formation, European Journal of Pharmaceutics and Biopharmaceutics, 69: 255-263 (2008).
Surana, A.S. and Kotecha, R.K., An Overview on Various Approaches to Oral Controlled Drug Delivery System via Gastroretention, International Journal of Pharmacological Science Reviews and Research, 2:68-72 (2010).
TENUATE® (diethylpropion hydrochloride USP immediate-release & diethylpropion hydrochloride USP controlled-release) package insert, 8 pages (2003).
Thaakur, S. and Himabindhu, G., Effect of alpha lipoic acid on the tardive dyskinesia and oxidative stress induced by haloperidol in rats, Journal of Neural Transmission, 116:807-814 (2009).
Torrado et al., Chitosan-poly(acrylic) acid polyionic complex: in vivo study to demonstrate prolonged gastric retention, Biomaterials, 25(5): 917-923 (2004).
USP Pharmacists' Pharmacopeia, 3 Supplement, Second Edition, 166 pages (2009).
Wilde, and Wagstaff, Acamprosate—A review of its pharmacology and clinical potential in the management of alcohol dependence after detoxification, Drugs, 53:1039-1053 (1997).
Written Opinion for PCT/US2014/041186, 10 pages (dated Sep. 26, 2014).
Guidance for Industry: Bioavailability and Bioequivalence Studies for Orally Administered Drug Products—General Considerations, U.S. Department of Health and Human Services Food and Drug Administration Center for Drug Evaluation and Research (CDER), 26 pages (2003).
Minipress Capsules (prazosin hydrochloride) for Oral Use, Distributed by Pfizer Labs (LAB-0212-4.0), 8 pages (Jul. 2009).

* cited by examiner

- NO FOOD EFFECT
- INDIVIDUAL VARIABILITY LESS THAN 25%
- ABOVE 100 ng/mL FOR AT LEAST 12H
- ABOVE 250 ng/mL FOR 6H
- IMPLICATION THAT STEADY-STATE PLASMA LEVELS WILL EXCEED THERAPEUTIC THRESHOLD >8 HOURS PER DAY WITH QD OR WITH BID DOSING IN MOST PATIENTS

ACAMPROSATE FORMULATIONS, METHODS OF USING THE SAME, AND COMBINATIONS COMPRISING THE SAME

CROSS-REFERENCE TO RELATED APPLICATION

This application is the National Stage of International Application No. PCT/US2014/041186, filed Jun. 5, 2014, which claims the benefit under 35 U.S.C. § 119(e) of U.S. Provisional Application No. 61/831,587, filed Jun. 5, 2013, the contents of each of which are incorporated herein in their entirety.

BACKGROUND

Acamprosate calcium (also referred to simply as "acamprosate"), the calcium salt of N-acetylhomotaurine, has been marketed for over 25 years as a treatment for alcoholism; specifically, it has been used to treat craving for alcohol in currently abstinent alcohol abusers. For this indication it has had limited effectiveness. Yahn S L, Watterson L R, Olive M F: Safety and efficacy of acamprosate for the treatment of alcohol dependence. Substance Abuse 7:1-12, 2013; Witkiewitz K, Saville K, Hamreus K: Acamprosate for treatment of alcohol dependence: mechanisms, efficacy, and clinical utility. Therapeutics and Clinical Risk Management 8: 45-53, 2012. Despite a number of positive clinical trials, and a few negative ones, the effectiveness of the drug in actual clinical use has been relatively low. In the United States, sales of the drug have been so low that its manufacturer has stopped actively marketing it.

While the effectiveness of acamprosate calcium for alcoholism has been disappointing, 25 years of use in many countries, with over one million patients, has established that the drug is extraordinarily safe for a central nervous system (CNS) drug. Virtually no severe adverse events unequivocally attributable to the drug have been reported.

Acamprosate is remarkable not only for its safety but for its mechanism of action, which is unique among CNS drugs currently approved in the United States. It modulates glutamate and GABA transmission, diminishing the former when it is excessive and increasing the latter when it is low, but not interfering meaningfully with normal neural traffic. It does this by indirect actions including the induction of protein synthesis within cells with glutamate receptors; it does not directly bind to primary glutamate or GABA receptors sites nor is it an allosteric modulator of those sites.

Because of its actions on glutamate and GABA transmission acamprosate can correct an imbalance of excitatory (glutamate-mediated) and inhibitory (GABA-mediated) neurotransmission. Such imbalances are currently thought to play a role in causing or influencing the severity of diverse neurological and psychiatric conditions including tardive dyskinesia (TD), levodopa-induced dyskinesia (LID), Tourette Syndrome (TS), obsessive-compulsive disorder (OCD), posttraumatic stress disorder (PTSD), tinnitus, autism, generalized anxiety, depression, and addictions to alcohol, nicotine, and cocaine. Several U.S. patents (e.g., U.S. Pat. Nos. 6,057,373, 6,294,583, 6,391,922, 6,689,816, and 7,498,361; each of which is incorporated herein by reference in its entirety) describe the use of acamprosate to treat neuropsychiatric disorders, including tardive dyskinesia and other movement disorders induced by chronic exposure of patients to neuroleptic (antipsychotic) drugs, Tourette's syndrome, and mental disorders such as posttraumatic stress disorder (PTSD) and obsessive-compulsive disorder (OCD).

SUMMARY

A drug with extraordinary safety and a unique mode of CNS action potentially applicable to highly prevalent neurological and psychiatric disorders would seem to be destined for great success. A new clinical entity with such a story would undoubtedly generate significant scientific and commercial interest. Acamprosate, however, has not had such success. The fact that it has been on the market and off-patent for a long time contributes to a lack of commercial interest. More fundamentally, though, acamprosate's usefulness as a treatment for CNS disorders is limited by the pharmacokinetic properties of the drug in its currently marketed formulation. That formulation, a 333 mg enteric-coated tablet (available under the trade name, Campral®), has poor and variable bioavailability (11% on average) that is further reduced if the drug is taken with food, and it has poor gastrointestinal (GI) tolerability. If a patient takes the drug with food to mitigate GI side effects the consequence will be less absorption of the drug. The labeled dose of two tablets three times daily probably does not produce therapeutically adequate plasma levels of the drug in many patients, while taking six pills a day on a three-time-daily (TID) basis is already a barrier to long-term treatment adherence, especially when patients are taking other drugs concurrently, and when the drug often causes gastrointestinal side effects.

Based upon the new innovation described herein, acamprosate has again become a clinically interesting drug—and perhaps a new option for treating CNS disorders. As set forth below and without being limited thereto, according to some embodiments acamprosate has been reformulated so that: (1) One or two pills daily can be an effective dose; (2) It can be taken with or without food with no adverse effect on bioavailability or efficacy; and/or (3) It infrequently has GI side effects, even when given at a significantly higher dosage per pill than the currently-marketed enteric-coated formulation.

The inventions herein show how acamprosate can be reformulated to attain one or more of these three properties. It might be thought that this would require increasing the bioavailability of the drug, and indeed some unsuccessful past attempts to reformulate acamprosate attempted to do this. Some embodiments described herein relate to how the three criteria for an improved formulation of acamprosate can be attained by tailoring the release kinetics of the formulation. By so doing GI side effects are mitigated, the food effect on pharmacokinetics (and not just bioavailability) is eliminated, and efficacy relative to the total daily milligram dose is increased. The new formulations created in this way are essentially new CNS drugs; the distinctive mechanism of action, remarkable safety, and potential for efficacy in a broad range of widely prevalent CNS disorders make them a salient therapeutic advance.

In one aspect, the present application describes new formulations and methods of using acamprosate that exhibit unpredictable and surprising properties. The new class of formulations addresses the drawbacks and limitations of the currently marketed formulation, Campral®, thereby facilitating the clinical use of acamprosate, alone or in combination with other drugs, for the treatment of neuropsychiatric disorders and other diseases and conditions. The new formulations can permit larger dosages of the drug in a single pill, better toleration with reduced and/or infrequent GI side effects, reduced or no food effect on bioavailability, similar bioavailability as Campral® taken without food, and significantly better bioavailability than Campral® is taken with food—thus better bioavailability than Campral® on its usual TID basis in which at least one of the doses is taken with food or shortly after eating.

Provided herein are sustained-release (SR) formulations of acamprosate. As used herein sustained-release formulations of acamprosate refer to the sustained-release (SR) formulations described herein and exemplified in Examples 3 and 4. In some embodiments the new formulations can give on average more than half of their 48-hour AUC in the first 12 hours after administration, while avoiding the high $C_{max}$ that would be produced by an immediate release (IR) preparation that give the same 12-hour AUC. In some embodiments, the formulations provided herein also have the remarkable, unexpected, and therapeutically valuable property of fed-fasting equivalence, i.e., of having substantially the same average AUC and $C_{max}$ in the fed state and in the fasting state. This property allows patients to take the formulation without consideration of food intake, and in particular with meals—either always or sometimes—if doing so is better tolerated and/or if it is more convenient. This improves treatment adherence, and because it does so with no negative impact on AUC or $C_{max}$, it can improve the effectiveness of the formulation as well as its efficacy.

The fed-fasting equivalence of formulations described herein was completely unpredictable and is remarkable. Given the known interference of food with the absorption of acamprosate, the site of sustained release of acamprosate from the SR tablet in the fed state must favor the extent and rate of acamprosate absorption to exactly the degree that the presence of food interferes with them. That these two factors should so exactly counterbalance each other was an unforeseen and wonderful discovery.

The formulations according to some embodiments retain their integrity for several hours in solution, releasing acamprosate by diffusion at a rate proportional to the square root of time. In some embodiments, without being limited thereto, the desirable release kinetics and fed-fasting equivalence of those kinetics, can result from such diffusion characteristics.

In some embodiments the new formulations or compositions include a high molecular weight polymer of acrylic acid, which also can be referred to as polyacrylic acid ("PAA"). Such polymers include a class of compounds called "carbomers," which include polymers with varying degrees of crosslinking, for example, with allyl ethers of polyalcohols. Examples of commercially available carbomers include those referred to as Carbopol® polymers (available from The Lubrizol Corporation, USA). Several examples of Carbopol® compounds that can be included with the new formulations are those available under the brand names Carbopol® 971P (carboxypolymethylene; carbomer homopolymer type A—lightly cross-linked with allyl ethers of pentaerythritol) and Carbopol® 974P (carboxypolymethylene; carbomer homopolymer type B—highly cross-linked with allyl ethers of pentaerythritol). The formulations further can include variable amounts of other pharmacologically suitable ingredients. In these compositions the weight of acamprosate may greatly exceed the total weight of the excipients, permitting the formulation of tablets small enough to easily swallow that contain significantly more acamprosate than any marketed formulation. (The largest dose of acamprosate calcium marketed in the US is 333 mg; a 500 mg pill is sold in other countries. By contrast, one example the formulations provided herein may contain 800 mg of acamprosate calcium in one tablet. The identification of a carbomer as a principal excipient, for some embodiments, to produce these kinetics was an unpredictable and surprising discovery. There are numerous choices for excipients for sustained release preparations and no a priori certainty that a particular one used at a particular ratio of API to excipient, with particular additional ingredients, will produce a specific desired in vivo pharmacokinetic profile, let alone result in fed-fasting equivalence of both $C_{max}$ and AUC when the API as an (immediate release) solution as well as the marketed product show a large food effect on drug absorption.

In some embodiments the compositions can include medications, such as neuroleptic (antipsychotic) and/or antidepressant drugs, combined with the improved acamprosate formulations. Also disclosed are methods of using the improved formulations or compositions in treating diseases and disorders, including movement disorders and other neuropsychiatric disorders. Some embodiments relate to improved compositions and methods of using the same where the compositions can be administered in either a fed or fasted state.

In one aspect, provided is a composition comprising less than or equal to about 1500 mg of a pharmaceutically acceptable salt of acamprosate and a carbomer polymer.

In some embodiments, the composition comprises less than about 1000 mg of the pharmaceutically acceptable salt of acamprosate. In some embodiments, the composition comprises about 800 mg of the pharmaceutically acceptable salt of acamprosate. In some embodiments, the composition comprises about 400 mg of the pharmaceutically acceptable salt of acamprosate. In some embodiments, the composition comprises about 1000 to 1500 mg of the pharmaceutically acceptable salt of acamprosate.

In some embodiments, the pharmaceutically acceptable salt of acamprosate is about 20% to about 90% of the total weight of the composition.

In some embodiments, the pharmaceutically acceptable salt of acamprosate is acamprosate calcium.

In some embodiments, the carbomer polymer is present at from about 1% to about 25% of the total weight of the composition. In some embodiments, the composition comprises about 10 mg to about 200 mg of the carbomer polymer. In some embodiments, the composition comprises the carbomer polymer is a cross-linked polyacrylic acid. In some embodiments, the carbomer polymer is Carbopol 971P. In some embodiments, the carbomer polymer is Carbopol 974P.

In some embodiments, the composition further comprises a first generation antipsychotic, a second generation antipsychotic, a selective serotonin reuptake inhibitor or a serotonin norepinephrine reuptake inhibitor. In some embodiments, the composition further comprises a second medication selected from the group consisting of thioridazine, chlorpromazine, thiothixene, trifluoperazine, fluphenazine, haloperidol, perphenazine, loxapine, molindone, metoclopramide, aripiprazole, asenapine, iloperidone, lurasidone, olanzapine, paliperidone, quetiapine, risperidone, ziprasidone, citalopram, desvenlafaxine, duloxetine, escitalopram, fluoxetine, fluvoxamine, milnacipran, paroxetine, sertraline, venlafaxine, or a combination thereof.

In another aspect, provided is a pharmaceutical composition comprising about 20% to about 90% by weight of pharmaceutically acceptable salt of acamprosate and an amount of a carbomer polymer sufficient to provide about 30% or more of the 48-hour AUC by 8 hours after administration.

In another aspect, provided is a unit dose of a pharmaceutical composition comprising up to about 1500 mg of acamprosate calcium or another pharmaceutically acceptable salt of acamprosate and an effective amount of a carbomer polymer, wherein the plasma exposure following a single dose of acamprosate is at least 100 ng/mL for 8 hours and is at least 250 ng/mL for 6 hours in a subject to whom the composition has been administered.

In some embodiments, the unit dose composition comprises less than about 1000 mg of the pharmaceutically acceptable salt of acamprosate. In some embodiments, the unit dose composition comprises about 800 mg of the pharmaceutically acceptable salt of acamprosate. In some embodiments, the unit dose composition comprises about 400 mg of the pharmaceutically acceptable salt of acamprosate. In some embodiments, the unit dose composition comprises about 1000 to 1500 mg of the pharmaceutically acceptable salt of acamprosate.

In some embodiments, the pharmaceutically acceptable salt of acamprosate is acamprosate calcium.

In some embodiments, the unit dose composition has been administered in the fasted state. In some embodiments, the unit dose composition has been administered in the fed state.

In another aspect, provided is a method of treating a disease, disorder, symptom, or syndrome in a patient in need of such treatment comprising administering to said patient the composition or unit dose composition described above.

In another aspect, provided is a method of treating a neuropsychiatric disorder in a patient, comprising administering to a patient a composition or unit dose composition described above.

In some embodiments, administration to the patient in a fed state and in a fasted state produces substantially bioequivalent acamprosate plasma $C_{max}$ values. In some embodiments, administration to the patient in a fed state and in a fasted state produces bioequivalent acamprosate plasma $T_{max}$ values. In some embodiments, administration to the patient in a fed state and in a fasted state produces bioequivalent acamprosate plasma AUC values.

In still another aspect, provided is a method of maintaining an in vivo steady-state acamprosate plasma concentration at or above a minimum level needed for therapeutic efficacy for a neuropsychiatric or other medical condition in a patient in need thereof, wherein the plasma concentration in steady state is above the minimum level at least 4-10 hours out of a 24 hour period, the method comprising administering to the patient a dosage of a pharmaceutically acceptable salt of acamprosate comprising up to about 1500 mg of acamprosate, and wherein the pharmaceutically acceptable salt of acamprosate is formulated in a polymer matrix that releases acamprosate by diffusion, and the dosage is administered either once daily or twice daily, either with or without food.

In some embodiments, the dosage comprises less than about 1000 mg of the pharmaceutically acceptable salt of acamprosate. In some embodiments, the dosage comprises about 400 mg of the pharmaceutically acceptable salt of acamprosate. In some embodiments, the dosage comprises about 800 mg of the pharmaceutically acceptable salt of acamprosate. In some embodiments, the dosage comprises about 1000 to 1500 mg of the pharmaceutically acceptable salt of acamprosate.

In some embodiments, the pharmaceutically acceptable salt of acamprosate is formulated in a polymer matrix that releases, by diffusion in vitro, approximately 50% of the acamprosate within 2 hours and releases at least 80% of the acamprosate within 4 hours.

In some embodiments, the steady-state in vivo acamprosate plasma concentration is maintained at or above a threshold for therapeutic efficacy for at least 4-10 hours out of a 24 hour period, wherein the therapeutic threshold is about 100 ng/mL to about 500 ng/mL.

In some embodiments, the steady-state in vivo acamprosate plasma concentration is maintained at or above a threshold for therapeutic efficacy for at least six hours out of a 24 hour period, wherein the therapeutic threshold is about 200 ng/mL. In some embodiments, the steady-state in vivo acamprosate plasma concentration is maintained at or above a threshold for therapeutic efficacy for at least six hours out of a 24 hour period, wherein the therapeutic threshold is about 300 ng/mL. In some embodiments, the in vivo acamprosate plasma level is at or above the therapeutic level for at least 8 hours.

In some embodiments, the pharmaceutically acceptable salt of acamprosate is acamprosate calcium.

In still another aspect, provided is composition comprising a pharmaceutically acceptable salt of acamprosate and a first generation antipsychotic or a second generation antipsychotic agent.

In some embodiments subject matter described in PCT/US2012/067507, filed Dec. 2, 2012 is specifically excluded, including one or more of the specific formulations described or claimed therein.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

Features, aspects, and advantages of the present invention will become apparent from the following description, and the accompanying exemplary embodiments shown in the drawings, which are briefly described below

FIG. 10 shows that the diffusion kinetics of tablets of Example 3 in different form are similar.

DETAILED DESCRIPTION

Figure 1:
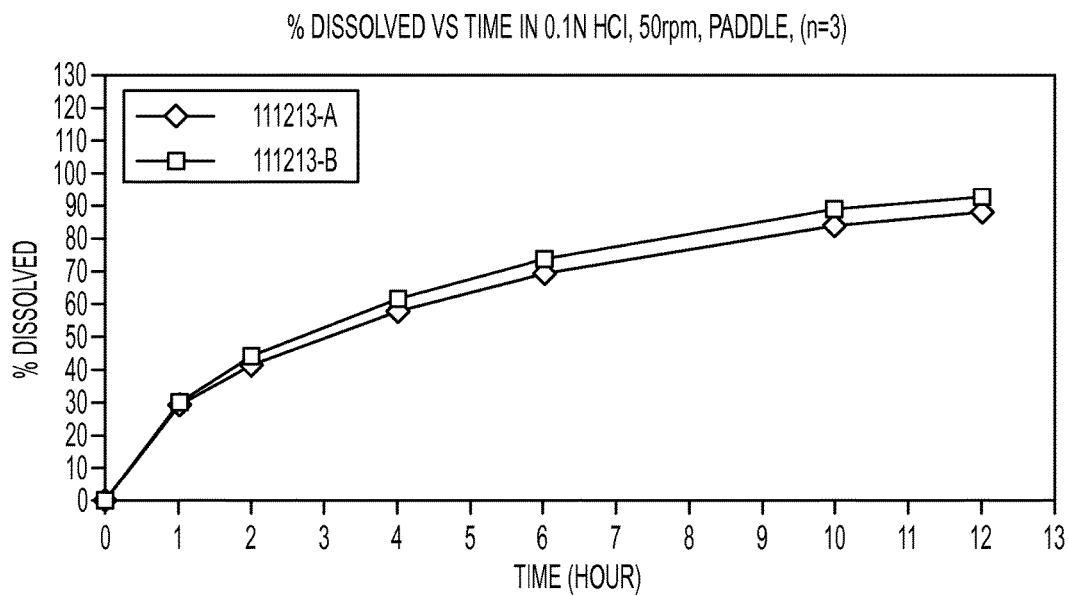
FIGS. 1-4 shows the release profile of tablets of Example 4 in acetate solution (pH 4.5) or 1M HCl (pH 1.0).
Figure 2:
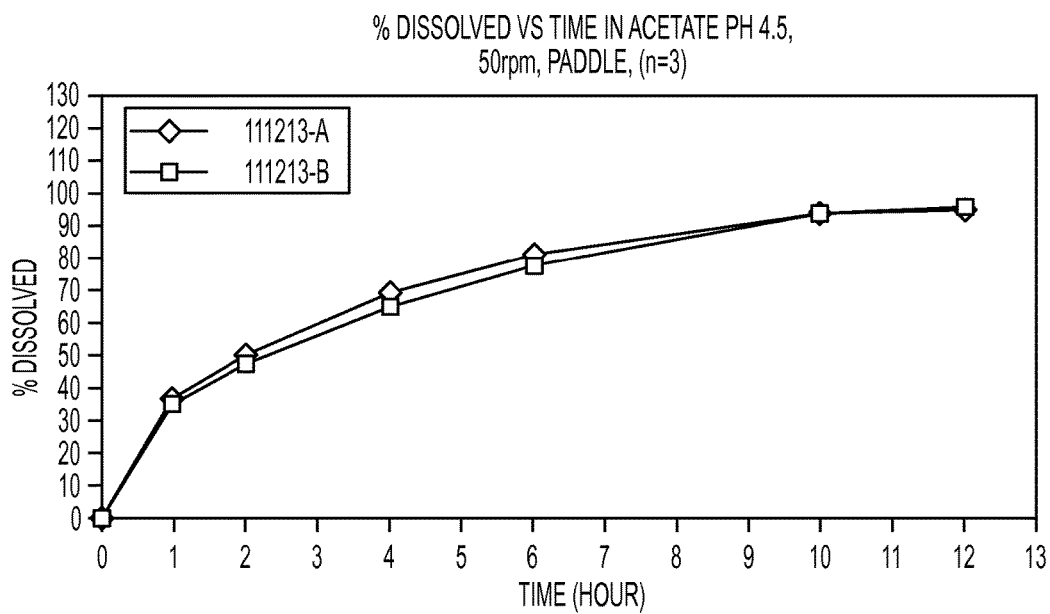
Figure 3:
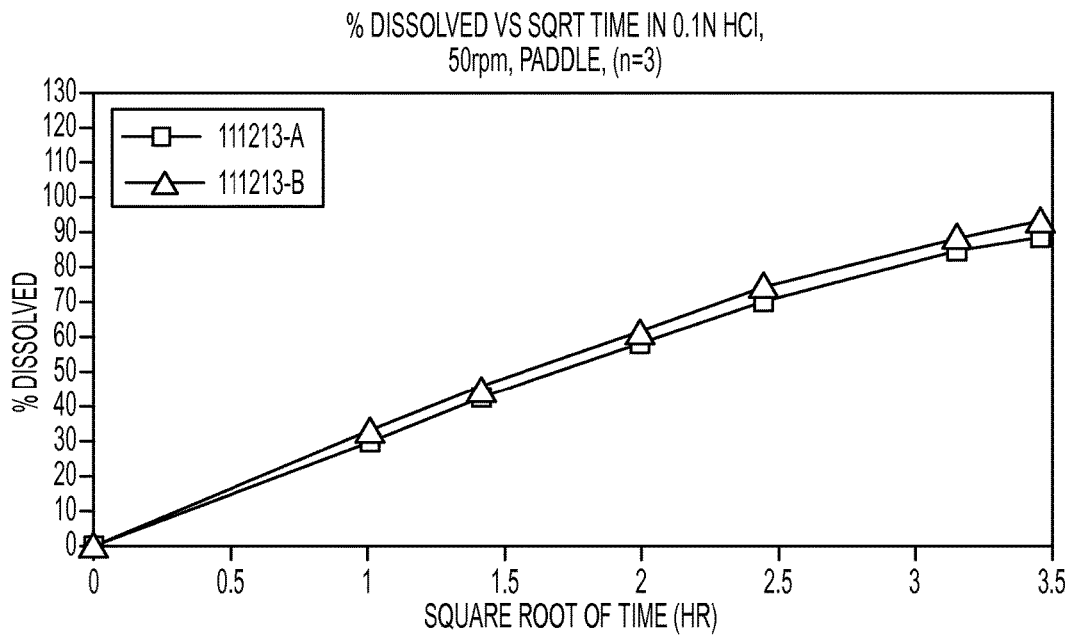
Figure 4:
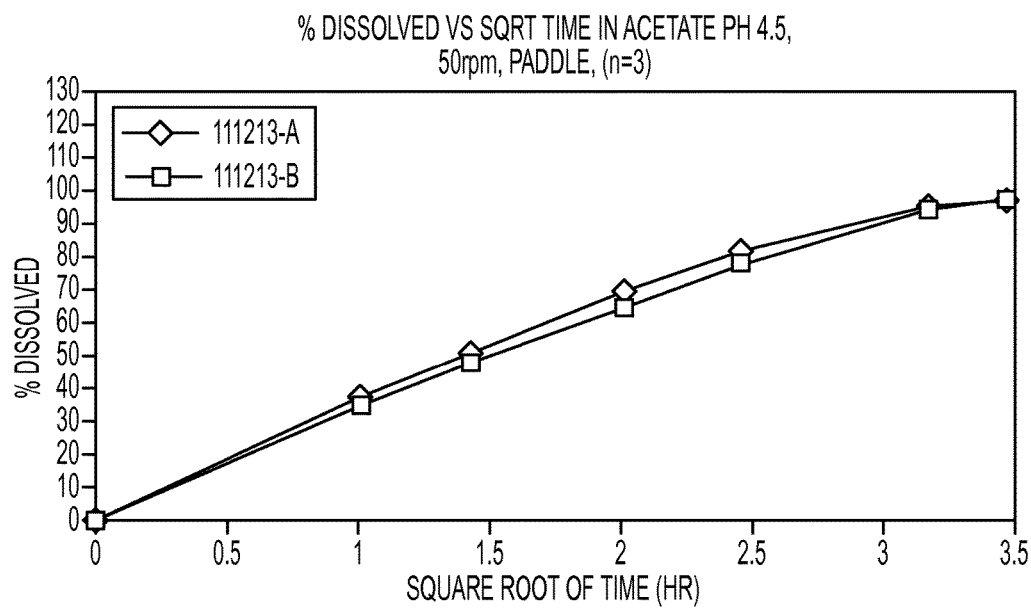

Acamprosate (bis acetyl-homotaurine; [3-(acetylamino)-1-propanesulfonic acid]; N-acetyl homotaurine) has effects on both glutamate-mediated and GABA-mediated neurotransmission. Acamprosate is a compound with high solubility and low permeability—Class III under the Biopharmaceuticals Classification System (BCS). The bioavailability of BCS Class III compounds tends to be low because the absorption of such compounds occurs either via diffusion—which is slow and inefficient because of the low permeability—or via specialized transporters in the membranes of intestinal mucosal cells—which may not exist, may poorly bind the compound, or may be easily saturated, implying zero-order kinetics. It is approved in several countries for the treatment of alcoholism—specifically, the inhibition of craving for alcohol in alcohol-dependent patients who are currently abstinent. Acamprosate has limited effectiveness for treating alcoholism. Some controlled studies have failed to show efficacy, and adoption of the drug in practice has not been widespread.

Acamprosate is commonly used in the form of its calcium salt. Other pharmaceutically acceptable salt of acamprosate can also be used. Such salts include acamprosate salts of inorganic bases, for example, alkaline metals such as sodium or potassium; salts of other alkaline earth metals such as magnesium; salts of organic bases, for example, trimethylamine, triethylamine, pyridine, picoline, ethanolamine, diethanolamine, triethanolamine. It should be understood that in the methods, uses and compositions described herein, that acamprosate calcium can be substituted for, by, or included with any other salt or analog, for example, one or more of sodium N-acetylhomotaurine, magnesium N-acetylhomotaurine, lithium N-acetylhomotaurine, or any other forms of N-acetylhomotaurine, at the same milligram dose and/or free acid equivalent dose. Unless otherwise stated, acamprosate refers to acamprosate calcium. However, this disclosure is not limited to acamprosate calcium and other pharmaceutically acceptable salts of acamprosate, such as those described above, can be used to substitute acamprosate calcium.

As noted above, the acamprosate calcium enteric-coated dosage form currently marketed in the United States is sold under the trade name Campral® and by various other trade names (e.g., Aotal™, Regtect™) in other countries. Each Campral® tablet contains 333 mg acamprosate calcium, which is equivalent to 300 mg acamprosate. These tablets are formulated as enteric coated tablets, with the labeled dose being 2 tablets, 3 times daily. It is noted on the label that taking Campral® with food impairs its bioavailability although the label does not require that the drug be taken without food.

As previously noted, embodiments herein generally relate to improved formulations of acamprosate, as well as to methods of using the same. Some embodiments relate to the unexpected and surprising discovery of new classes of formulations that provide various unexpected advantages, as discussed more fully herein. In some aspects the improved formulations and methods can permit the use of acamprosate to treat various disorders while permitting one more of the following (without being limited thereto): (1) the use of the compositions in either a fed or a fasted state with equal therapeutic efficacy, which is a new discovery; (2) the use of lower total daily dosages, fewer administrations per day and/or fewer pills per administration, which can lead to greater compliance and greater efficacy; (3) less frequent and/or less severe gastrointestinal side effects; and (4) the use of acamprosate (or another pharmacologically-acceptable salt of N-acetylhomotaurine) in combination formulation with another medication, which was not feasible or practicable prior to the instant compositions and methods. The compositions and methods are described in additional detail herein.

Definitions

The term "subject" or "patient" as used herein, refers to any animal such as a human.

The term "treating," "treat," "treatment" or the like, refers to any or all of an alleviation or elimination of one or more symptoms associated with a disease, disorder, or condition, halt or slowing of further progression or worsening of the disease, disorder, or condition, including its symptoms, or prevention or prophylaxis of the disease, disorder, or condition, such as reducing the risk of or delaying the occurrence of the disease, disorder, or condition in a subject determined to be predisposed to the disease, disorder, or condition but not yet diagnosed as having the disease, disorder, or condition. For example, within the context of tardive dyskinesia (TD), treatment may include an alleviation of symptoms of TD, such as involuntary, irregularly rhythmic movements, or halting or slowing the progression of the disease, as measured by a reduction or cessation of the involuntary, irregularly rhythmic movements or preventing the worsening of symptoms relating to the aging of the patient or the discontinuation of antipsychotic medication, or prevention or prophylaxis of TD, such as reducing the risk of occurrence or worsening of TD in a subject who is on an antipsychotic drug or other dopamine receptor blocking drug for a period of time.

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Embodiments defined by each of these transition terms are within the scope of this invention.

The term "about" as used herein in conjunction with a stated numerical value, refers to a value within ±10%, ±5% or ±1% of the stated numerical value.

The term "substantially" means within 80% to 120%, or 90% to 110%, or 95% to 105% range of a reference value or any sub value or sub range there between.

The term "substantially equivalent" or "substantially the same" or the like when describing a value, such as release rate, means that at the same relative time point the value does not differ by more than 1% to 20% or any sub value or sub range there between (e.g., 5%, 10%, 20%, etc.). For example, when the release rate of a composition in a pH 1.0 solution is from about 80% to 120% of the release rate of the composition in a pH 4.5 solution when measured at the same time point calculated from the time when the composition is added to the solutions, then the composition has a substantially equivalent release rate at pH 1.0 and pH 4.5 at that particular time point. If the composition had an equivalent release rate at pH 1.0 and pH 4.5 at no less than 90% of the total time points within the range of determination, then the composition would be said to have an equivalent release profile at pH 1.0 and pH 4.5. In some embodiments when describing a PK profile, such as $T_{max}$, $C_{max}$, or AUC, two values are considered to be substantially the same if they meet the bioequivalence definition as set forth by a regulatory agency, such as the U.S. Food and Drug Administration (FDA), the European Medicines Agency (EMA), and the Australian Therapeutics Goods Administration (TGA).

The term "substantially intact" means that the shape and size of the composition (such as a pill or tablet) remain substantially the same as the original shape and size of the composition in that each dimension is within 80% to 120%, or 90% to 110%, or 95% to 105% range of corresponding original dimension, or any sub value or sub range there between.

The term "AUC" is an abbreviation for "area under the curve" in a graph of the acamprosate concentration over time in a certain part or tissue, such as blood or plasma or, if applicable, in another body fluid such as cerebrospinal fluid, of a subject to whom acamprosate has been administered.

The term "$C_{max}$" is an abbreviation that refers to the maximum observed concentration of acamprosate in a certain part or tissue, such as blood or plasma (or, if applicable, in another body fluid), of a subject to whom acamprosate has been administered.

The term "$T_{max}$" is an abbreviation that refers to the time point when the time the maximum observed concentration of acamprosate is reached in a certain part or tissue, such as blood or plasma or, if applicable, in another body fluid, of a subject to whom acamprosate has been administered.

The term "$T_{1/2}$" is an abbreviation that refers to the time period required for the concentration of acamprosate in blood or plasma (or, if applicable, in another body fluid), to fall to one-half of its initial value, in the absence of administration of any additional drug.

Unless otherwise specified, the various in vitro dissolution values, and pharmacokinetic values, such as AUC, $C_{max}$, $T_{max}$, $T_{1/2}$, release rate, etc., used herein are average values of a typical population of subjects and the values of a particular individual subject may vary as can be appreciated by a person skilled in the art.

The term "other medication" refers to any compound or composition that is approved or will be approved for administration to a human in any manner by any regulatory agency, such as the FDA, EMA and TGA. In some embodiments, the other medication is not contraindicated for acamprosate. In some embodiments, the other medication is a medication for the treatment of a disease which acamprosate is intended to treat.

The term "confidence interval" or "CI" as used herein has its ordinary meaning, such as used in defining bioequivalence by a regulatory agency, such as the FDA, EMA and TGA. A confidence interval is specified by the percentage of cases that lie within the interval.

The term "fed state" refers to a state of a subject wherein there is food in the stomach of the subject such that the release and/or absorption of acamprosate from the a formulation can be affected as compared with when there is no food in the stomach. In some embodiments, a fed state is the state of the subject during the time from the start of food consumption to about 2 hours after food consumption, such as during food consumption, immediately after food consumption, about 30 minutes after food consumption, about 1 hour after food consumption, about 1.5 hours after food consumption, or about 2 hours after food consumption, or any time between any of the two numbers, end points inclusive. As used herein, food consumption refers to consuming a substantial amount of food, such as at least one third of a normal meal of a subject, either by volume or by total number of calories consumed.

The term "fasted state" refers to a state of a subject wherein there is substantially no residual food in the stomach of the subject. In some embodiments, a fasted state is the state of the subject during the time from about 2-3 hours after food consumption to about 30 minutes before the next food consumption, such as 3 hours after food consumption, 3.5 hours after food consumption, 4 hours after food consumption, or 30 minutes before the next food consumption, or any time between any of the two numbers, end points inclusive.

Formulations

As already noted above, various embodiments relate to formulations comprising acamprosate. For example, some embodiments relate to unit dosage forms and pharmaceutical compositions comprising acamprosate calcium or another pharmaceutically acceptable salt thereof, and methods of treatment using the same.

A sufficient brain level of acamprosate is needed for treating certain disorders such as craving in abstinent alcoholics or neuropsychiatric disorders such as tardive dyskinesia and other movement disorders. However, the brain levels needed for therapeutic effect in these conditions are in many subjects difficult to attain using existing formulations, such as the marketed formulation (Campral®) without giving total daily dosages of 2-4 grams or more. If administered three times per day (TID), this daily dosage of Campral® would require two to four 333 mg pills per administration. Such doses are burdensome and create treatment adherence issues. Further, the existing dosage forms have poor gastrointestinal (GI) tolerability with patients complaining of nausea, vomiting, and diarrhea, and many discontinuing the medication or taking it irregularly because of the side effects. For example, the c package insert reports that 10% of patients taking 1332 mg per day of Campral® had diarrhea and 17% of patients taking 1998 mg a day (two 333 mg tablets TID) had diarrhea; overall, 28% of patients taking Campral® had a GI side effect of some kind.

Poor tolerability of taking Campral® that causes GI irritation may be improved by taking the medication with meals. However, in the case of the Campral® formulation, taking the medication with food reduces its bioavailability by approximately 23% and its $C_{max}$ by approximately 42%, implying a substantial effect on the residence time of the drug at a potentially therapeutic blood level. In another study, it was found that both bioavailability and $C_{max}$ in the first 48 hours reduced by about 41% on average when the Campral® formulation was taken in a fed state than in a fasted state. In particular, the significantly reduced $C_{max}$ may result in that the plasma concentrations of acamprosate will not be within a therapeutically effective range when a normal dosage of the Campral® formulation is administered in a fed state. All of these factors lead to Campral® being a less than ideal formulation of acamprosate for the treatment of neuropsychiatric conditions.

Some embodiments herein relate to formulations of acamprosate that can attain adequate central nervous system (CNS) levels of the drug, are well tolerated, and can be administered once or twice a day. In some aspects, the formulations permit the administration of a single pill or tablet once or twice a day. In some aspects the formulations can include more than 333 mg or more than 500 mg of acamprosate calcium in a single pill. Such formulations can contain a large amount of acamprosate, yet can be swallowed easily, and/or can have good GI tolerability.

Accordingly, some embodiments described herein relate to the surprising and unexpectedly effective discovery of formulations suitable, for example, as pills or tablets that have more than 333 mg or more than 500 mg of acamprosate calcium and have a reasonable size that can be swallowed. Such embodiments include a combination of excipients that provide the pill or tablet with physical integrity and desired release kinetics with the least mass and volume. Surprisingly, such compositions comprising up to 800 mg or more (such as 1.5 g) of acamprosate calcium in a tablet that is small enough to swallow can be obtained using formulations that maintain their integrity for a sufficient period of time and release the active ingredient at rate substantially equal to the square root of time.

In some embodiments, the formulations include a polymer such as a polyacrylic acid polymer, preferably carbomers. As noted above, carbomers include acrylic acid polymers with varying degrees of crosslinking, for example, with allyl ethers of polyalcohols.

In some embodiments, carbomers can be depicted as

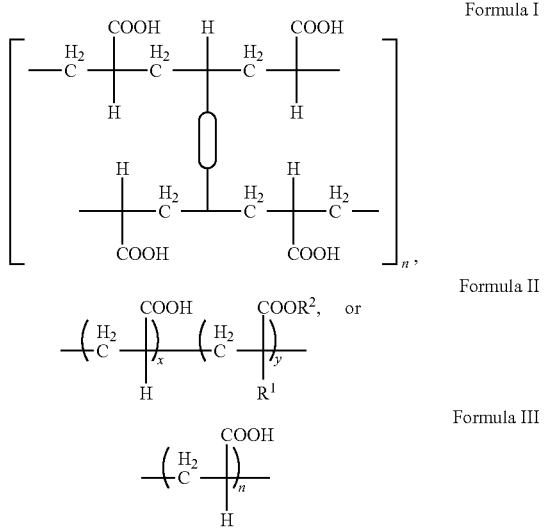

⊂⊃ is cross linking group, such as alkylene, allylsucrose or allyl pentaerythritol, each $R^1$ is independently hydrogen or $CH_3$, each $R^2$ is independently hydrogen or $C_1$-$C_{30}$alkyl, and x, y and n are independently an integer which can be as much as to produce a polymer having a molecular weight of up to 4.5 billion. Formulas II and III can be cross-linked with a cross linking group such as alkylene, allylsucrose or allyl pentaerythritol.

In some embodiments, the average molecular weight of carbomer is about 10,000 to 1,000,000, such as about 10,000, 50,000, 100,000, 200,000, 500,000, 700,000, 1,000,000, or any ranges between two of the values, end point inclusive. In some embodiments, n is a integer of 500 to 5000, 1000-2000, 2000-3000, 3000-4000, or 4000-5000, or any value or subrange therebetween.

Examples of commercially available carbomers include those referred to as Carbopol® polymers (available from The Lubrizol Corporation, USA). Several non-limiting examples of Carbopol® compounds that can be included with the new formulations are those available under the brand names Carbopol® 971P (carboxypolymethylene; carbomer homopolymer type A—lightly cross-linked with allyl ethers of pentaerythritol) and Carbopol® 974P (carboxypolymethylene; carbomer homopolymer type B—highly cross-linked with allyl ethers of pentaerythritol). The formulations further can include additional excipients and ingredients. Additional polymers optionally can be included such as carboxymethylcellulose (CMC).

Without being limited thereto, it is worth noting that such formulations surprisingly and unexpectedly can provide a number of advantages. For example, in some non-limiting aspects, the formulations can permit the administration of acamprosate with or without food, or in a fed or a fasted state, with an equal expectation of therapeutic efficacy In some non-limiting aspects the formulations can provide substantially equivalent pharmacokinetics, and substantial equivalence in therapeutic efficacy. Such a discovery is quite unexpected in view of the fact that existing formulations have been reported to have significant (e.g., 23% or more) decrease in bioavailability in the presence of food, which can lead to poorer therapeutic efficacy, and data from a pharmacokinetic study of Campral® in healthy male volunteers reported herein suggests that the 23% reported decrease in bioavailability in the fed state may be an underestimate in populations of clinical interest.

Accordingly, in one aspect, the technology described herein provides a unit dose of a pharmaceutical composition comprising up to 1.5 grams of a pharmaceutically acceptable salt of acamprosate and a carbomer polymer. In some embodiments, the pharmaceutically acceptable salt of acamprosate is acamprosate calcium. The dosage form can be in an oral form, such as a pill or tablet or any other embodiment that can be swallowed by the patient.

In some embodiments, the composition may include, for example, about 400 mg to 1500 mg or about 600 mg to 1500 mg of acamprosate or pharmaceutically acceptable salt thereof (or any value or ranges between any two numbers, end points inclusive). For example, the amount of acamprosate (or a pharmaceutically acceptable salt thereof) can be about 400 mg, about 500 mg, about 600 mg, about 700 mg, about 800 mg, about 900 mg, about 1000 mg, about 1100 mg, about 1200 mg, about 1300 mg, about 1400 mg, about 1500 mg. In some embodiments, the unit dose of a pharmaceutical composition can include less than about 1000 mg of acamprosate or a pharmaceutically acceptable salt thereof.

In some embodiments, the acamprosate calcium or another pharmaceutically acceptable salt thereof is about 20% to about 95% of the total weight of the composition (or any value or range between those numbers, end points inclusive). In some embodiments, the acamprosate calcium or another pharmaceutically acceptable salt thereof is about 20%, about 30%, about 40%, about 50%, about 60%, about 70%, about 72%, about 75%, about 80%, or about 90% of the total weight of the composition, or any value or ranges between any two of the numbers (end points inclusive).

As noted above, in some embodiments, the carbomer polymer is a cross-linked polyacrylic acid. In some embodiments, the carbomer polymer is carbomer homopolymer Type A. In some embodiments, the carbomer polymer is carbomer homopolymer Type B. In some embodiments, the carbomer is a carbomer having viscosity of from about 4,000 to about 39,400, or from about 4,000 to about 11,000, or from about 29,400 to about 39,400 cP as a 0.5 wt % aqueous solution at pH 7.3-7.8. In some embodiments, the carbomer polymer is Carbopol® 971P, available from The Lubrizol Corporation, USA. In some embodiments, the carbomer polymer is Carbopol® 974P, available from The Lubrizol Corporation, USA.

In some embodiments, the unit dose of a pharmaceutical composition comprises the carbomer in an amount that provides a $T_{max}$ of 1-4 hours in the fasting state, and 2-5 hours in the fed state, a human to whom the composition has been administered.

In some embodiments, the carbomer polymer is present at from about 1% to about 30% of the total weight of the composition (or any value or range there between, end points inclusive). In some embodiments, the polyacrylic acid polymer or the carbomer polymer is present at about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% of the total weight of the composition, or any value or ranges between any two of the numbers (end points inclusive).

In some embodiments, the unit dose of the pharmaceutical composition comprises about 10 mg to about 300 mg of the carbomer polymer (or any value or range there between, end points inclusive). In some embodiments, unit dose comprises about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, or about 200 mg of the carbomer polymer, or any ranges between any two of the numbers (end points inclusive).

In some embodiments, provided is a unit dose of a pharmaceutical composition comprising up to about 1500 mg of acamprosate calcium, or another pharmaceutically acceptable salt thereof, and an effective amount of a carbomer polymer, wherein the plasma exposure in a human following administration of the unit dose to the human is at least 100 ng/mL for 8 hours and is at least 250 ng/mL for 6 hours. In some embodiments, the plasma exposure is at least 150 ng/mL for 8 hours, at least 200 ng/mL for 8 hours, at least 250 ng/mL for 8 hours, or at least 300 ng/mL for 6 hours, or a range between any two of the plasma exposure values, end points inclusive.

In some embodiments, the unit dose of the composition can be administered in the fasted state. In some embodiments, the unit dose of the composition can be administered in the fed state. In some embodiments administration in one of the fed or fasted states can specifically be excluded. In some embodiments the unit dose can be administered for therapeutic purposes in either the fed or the fasted state, with the subject having the option for each individual dose as to whether to take it with or without food. In some embodiments the unit dose of the composition can be administered immediately prior to food intake (e.g., within 30 or within 60 minutes before), with food, right after food intake (e.g., within 30, 60 or 120 minutes after food intake). In some embodiments, it can be administered, for example, at least 2 hours, 3 hours, 4 hours, 5 hours, 6 hours, 7 hours, 8 hours, 9 hours, 10 hours, 11 hours, 12 hours, or more after food intake, or any time there between. In some embodiments, the unit dose of the composition is administered after overnight fasting. In some embodiments the unit dose of the composition can be administered 30 minutes before food intake, 1 hour, 2 hours, 3 hours, 4 hours, 5 hours, 6 hours, 7 hours, 8 hours, 9 hours, 10 hours, 11 hours, 12 hours or more before food intake, or any time there between.

In some embodiments, the formulation provide substantially the same (bioequivalent) release profile of acamprosate whether administered in a fed or fasted state, with or without food, or at any time described above.

In some embodiments, provided is a composition comprising about 20% to about 90% by weight of acamprosate or another pharmaceutically acceptable salt of N-acetylhomotaurine and an amount of a carbomer polymer sufficient to provide a $T_{max}$ of acamprosate in plasma from about 1 hours to about 6 hours. In some embodiments, provided is a composition comprising up to about 800 mg of a pharmaceutically acceptable salt of acamprosate, which is about 20% to about 90% by weight of the total weight of the composition, and an amount of a carbomer polymer sufficient to provide a plasma $C_{max}$ of acamprosate from about 200 ng/mL to about 500 ng/mL. In some embodiments, provided is a composition comprising up to about 1200 mg of a pharmaceutically acceptable salt of acamprosate, which is about 20% to about 90% by weight of the total weight of the composition, and an amount of a carbomer polymer sufficient to provide a plasma $C_{max}$ of acamprosate from about 200 ng/mL to about 750 ng/mL.

In some embodiments, the unit dose or the pharmaceutical composition may further include a swellable hydrophilic polymer. Such polymers swell rather than dissolve when in contact with water. Examples of swellable hydrophilic polymers include cellulosic hydrocolloids such as methylcellulose (MC), hydroxypropylcellulose (HPC), hydroxymethylcellulose (HPMC), hydroxy-ethylcellulose (HEC), carboxymethylcellulose (CMC), carboxymethylcellulose sodium (NaCMC) and carboxyethylcellulose (CEC), or mixtures thereof. In one embodiment, the swellable hydrophilic polymer is carboxymethylcellulose.

In some embodiment, the unit dose or pharmaceutical composition further comprises a suspension agent, such as crosscarmellose.

In some embodiments, the formulations does not include one or more absorption-promoting agents. In some embodiments, the absorption-promoting agent can be one or more lipid substances selected from polysorbates, ethers of polyoxyethylene and alkyl, esters of polyoxythylene and fatty acids, fatty alcohols, bile acids and their salts with pharmaceutically acceptable cations, esters of $C_1$-$C_6$ alkanols with fatty acids, esters of a polyol with fatty acids wherein said polyol comprises 2 to 6 hydroxyl groups, and polyglycolysed glycerides. In some embodiments, the absorption-promoting agent has a hydrophilic-lipophilic balance (HLB) value of greater than 8. It should be understood that in some embodiments the formulations can specifically exclude an absorption promoting agent, including one or more absorption-promoting agents described herein.

The unit dose or the pharmaceutical composition may further include an elastomer. Suitable elastomers are known in the art and include, thermoplastic polyurethane elastomers or thermoplastic polycarbonate-urethanes, e.g., Carbosil® (thermoplastic silicone polycarbonate polyurethane available in several versions from DSM Biomedical, USA).

The unit dose or the pharmaceutical composition may further include a glidant. Suitable glidants are known in the art and include silicon dioxide, colloidal silicon dioxide, fumed silicon dioxide, calcium silicate, corn starch, magnesium carbonate, asbestos free talc, metallic stearates, calcium stearate, magnesium stearate (MGST), zinc stearate, stearowet C™, starch, starch 1500, magnesium lauryl sulfate, and magnesium oxide, or mixtures thereof. In one embodiment, the glidant is colloidal silicon dioxide. In some embodiments, the colloidal silicon dioxide is present in the composition in an amount of 0.01 to about 10.0% w/w, about 0.05 to about 5.0% w/w, about 0.02 to about 3.0% w/w, or about 0.1 to about 1.5% w/w.

The unit dose or the pharmaceutical composition may further include a lubricant. Suitable lubricants are known in the art and include magnesium stearate, calcium stearate, sodium stearyl fumarate, stearic acid, hydrogenated vegetable oil, glyceryl behenate, and polyethylene glycol, or mixtures thereof. In one embodiment, the lubricant is magnesium stearate. In some embodiments, the magnesium stearate is present in the composition in an amount of about 0.01 to about 10.0% w/w, about 0.1 to about 5.0% w/w, about 0.2 to about 3.0% w/w, or about 0.25 to about 1.5% w/w.

The unit dose or the pharmaceutical composition may further include a disintegrant or a supplemental binder. Suitable disintegrants are known in the art and include crosscarmellose sodium, sodium starch glycolate, crospovidone, microcrystalline cellulose, pregelatinized starch, cornstarch, alginic acid, and ion exchange resin. In one embodiment, the disintegrant is Starcap® 1500 (co-processed mixture of globally accepted excipients, corn starch and pregelatinized starch; available from Colorcon, USA).

In some embodiments, the unit dose or the pharmaceutical composition comprises, consists essentially of, or consists of a high molecular weight swellable polymer, such as carbomer (e.g., Carbopol 974P® or Carbopol 971P®), and one or more excipients selected from microcrystalline cellulose (e.g., Avicel PH102 or Avicel PH10), carboxymethylcellulose (e.g., CMC 7HF), vinyl pyrrolidone, Povidone K-90, silicon dioxide (e.g. Cabosil), colloidal silicon dioxide, fumed silicon dioxide, calcium silicate, magnesium carbonate, asbestos free talc, talc, metallic stearates, citric acid, calcium stearate, magnesium stearate, zinc stearate, starch (e.g., StarCap 1500), starch 1500, magnesium lauryl sulfate, magnesium oxide, and water. In one embodiment microcrystalline cellulose is present in an amount of about 5 to about 40% weight/weight (w/w), such as about 5, about 10%, about 15%, about 20%, about 25%, about 30%, about 35%, about 40% or any ranges between any two of the values, end points inclusive. In some embodiments, each of colloidal silicon dioxide, citric acid, carboxymethylcellulose, starch, talc, magnesium stearate, vinyl pyrrolidone, and silicon dioxide, if present, is present in the composition in an amount of 0.01 to about 10.0% w/w, about 0.05 to about 5.0% w/w, about 0.02 to about 3.0% w/w, or about 0.1 to about 1.5% w/w.

The unit dose or the pharmaceutical composition may be provided in the form of a tablet, a film coated tablet, a pill, a gel cap, a caplet, or a bead. In one embodiment, the composition is in the form of a spherical disc shaped tablet. In one embodiment, the composition is in the form of an oval shaped tablet. In one embodiment, the composition is in the form of an oblong shaped tablet.

In some embodiments, the pharmaceutical composition described herein further comprises one or more other medications, such as a first generation antipsychotic, a second generation antipsychotic, a selective serotonin reuptake inhibitor (SSRI) or a serotonin-norepinephrine reuptake inhibitor (SNRI). In some embodiments, the pharmaceutical composition described herein can be administered with one or more other medications, such as a first generation antipsychotic, a second generation antipsychotic, a selective serotonin reuptake inhibitor or a serotonin norepinephrine reuptake inhibitor.

For example, a composition as described herein can further comprise or be administered with at least a second medication that includes one or more of an antipsychotic (neuroleptic) medication, a selective serotonin reuptake inhibitor (SSRI), a serotonin-norepinephrine reuptake inhibitor (SNRI), an antidepressant other than an SSRI or SNRI, an anti-anxiety medication other than an SSRI or SNRI or the like; or the anti-nausea drug metoclopramide The antipsychotic medication can be, for example, a first or a second generation antipsychotic. The first or a second generation antipsychotic can be for example, one or more of thioridazine, chlorpromazine, thiothixene, trifluoperazine, fluphenazine, haloperidol, perphenazine, loxapine, molindone, aripiprazole, asenapine, iloperidone, lurasidone, olanzapine, paliperidone, quetiapine, risperidone, ziprasidone, and the like. The SSRI or SNRI can be, for example, one or more of citalopram, desvenlafaxine, duloxetine, escitalopram, fluoxetine, fluvoxamine, milnacipran, paroxetine, sertraline, venlafaxine, and the like. The product may include, for example, a single dosage form unit that includes, consists or consists essentially of both acamprosate and at least one second medication.

In some embodiments, the pharmaceutical composition described herein further comprises one or more other medications are selected from the group consisting of thioridazine, chlorpromazine, thiothixene, trifluoperazine, fluphenazine, haloperidol, perphenazine, loxapine, molindone, aripiprazole, asenapine, iloperidone, lurasidone, olanzapine, paliperidone, quetiapine, risperidone, ziprasidone, citalopram, desvenlafaxine, duloxetine, escitalopram, fluoxetine, fluvoxamine, milnacipran, paroxetine, sertraline, venlafaxine or metoclopramideor a combination thereof. In some embodiments, the pharmaceutical composition described herein can be administered with one or more other medications selected from the group consisting of thioridazine, chlorpromazine, thiothixene, trifluoperazine, fluphenazine, haloperidol, perphenazine, loxapine, molindone, aripiprazole, asenapine, iloperidone, lurasidone, olanzapine, paliperidone, quetiapine, risperidone, ziprasidone, citalopram, desvenlafaxine, duloxetine, escitalopram, fluoxetine, fluvoxamine, milnacipran, paroxetine, sertraline, venlafaxine, or metoclopramide, or other medications described herein, or a combination thereof.

In some embodiments, the composition of acamprosate described herein further comprises prazosin. In some embodiments, prazosin is in the amount of from about 1 mg to 15 mg, such as about 1 mg, 5 mg, 10 mg, or 15 mg, or any ranges between any two values. In some embodiments, acamprosate is in the amount of from about 400 mg to 1500 mg, such as about 400 mg, 500 mg, 800 mg, 1000 mg, 1300 mg, or 1500 mg, or any ranges between any two values. Prazosin (trade names Minipress®, Vasoflex®, Pressin® or Hypovase®) is a sympatholytic drug used to treat high blood pressure and anxiety, PTSD, and panic disorder. It is an alpha-adrenergic blocker that is specific for the alpha-1 receptors. Combining prazosin with the acamprosate sustained release formulation described herein may enhance its central nervous system (CNS) levels relative to its systemic levels, as prazosin is both a substrate of and an inhibitor of the ABCG2 efflux pump, which determines the level of prazosin in the CNS. The enhanced CNS levels may reduce the hypotension seen early on in treatment with that prazosin, mitigate prazosin food effect, or improve the efficacy of prazosin. In some embodiments, In some embodiments, the composition of acamprosate described herein further comprises a second-generation neuroleptic, such as lamotrigine, quetiapine, neuroleptic.

In some embodiments, the combination is in a single composition, for example, a bilayer composition wherein each layer comprising one medication.

The unit dose or the pharmaceutical composition can be prepared by methods known in the art, such as via melt pelletization, melt-granulation, or melt-extrusion techniques.

The unit dose or the pharmaceutical composition may further comprise a coating. Many coatings for tablets are generally known in the art, and any suitable coating can be utilized.

The unit dose or the pharmaceutical composition as described herein may optionally be coated with one or more coatings. In some embodiments, the sustained release formulation described herein that further comprises a second medication may contain a coating that freely allows the passage of acamprosate but would limit and control the release of the second medication. For instance, a coating can be added that provides for either pH-dependent or pH-independent release of the second medication, e.g., when exposed to gastrointestinal fluid. When a pH-independent coating is desired, the coating is designed to help achieving optimal release regardless of pH-changes in the environmental fluid, e.g., the GI tract.

Cellulosic materials and polymers, including alkylcelluloses, are sustained release materials well suited for coating the substrates, e.g., pills, tablets, etc.

In other embodiments, the coating can include a pharmaceutically acceptable acrylic polymer.

Kits

In another aspect, provided is a kit comprising a composition comprising acamprosate calcium or another pharmaceutically acceptable salt of acamprosate described herein and a label instruction of administering the composition with or without food.

In another aspect, provided is a kit comprising a composition comprising acamprosate calcium or another pharmaceutically acceptable salt of acamprosate described herein and a pharmaceutical composition of a second medication. In some embodiments, the kit further comprises a label instruction of administering the compositions together. In some embodiments, the kit further comprises a label instruction of administering the composition comprising a composition comprising acamprosate calcium or another pharmaceutically acceptable salt of acamprosate with or without food. In some embodiments, the kit further comprises a label instruction of administering the composition comprising acamprosate calcium or another pharmaceutically acceptable salt of acamprosate with food if the second medication is to be administered with food. In some embodiments, the kit further comprises a label instruction of administering the composition comprising acamprosate calcium or another pharmaceutically acceptable salt of acamprosate without food if the second medication is to be administered without food. In some embodiments, the kit is a blister pack comprising a unit dose of the acamprosate composition and an associated dose of the composition of the second medication. Such a package is contemplated to facilitate optimization of the dose of the second medication.

In some embodiments, the second medication is prazosin.

In some embodiments, the second medication is one or more antipsychotic (neuroleptic) medications, such as first or a second generation antipsychotic. First generation antipsychotic include: chlorpromazine, chlorprothixene, levomepromazine, mesoridazine, periciazine, thioridazine, loxapine, molindone, perphenazine, thiothixene, droperidol, flupentixol, fluphenazine, haloperidol, pimozide, prochlorperazine, trifluoperazine, and zuclopenthixol. Second generation antipsychotic include amisulpride, aripiprazole, asenapine, blonanserin, clozapine, iloperidone, lurasidone, melperone, olanzapine, paliperidone, quetiapine, risperidone, sertindole, sulpiride, ziprasidone, and zotepine.

In some embodiments, the second medication is one or more selective serotonin reuptake inhibitors (SSRI), such as citalopram, escitalopram, fluoxetine, fluvoxamine, paroxetine and sertraline.

In some embodiments, the second medication is one or more serotonin-norepinephrine reuptake inhibitors (SNRI), such as bicifadine, desvenlafaxine, duloxetine, levomilnacipran, milnacipran, sibutramine and venlafaxine.

In some embodiments, the composition of acamprosate described herein further comprises a second-generation neuroleptic, such as lamotrigine, quetiapine, neuroleptic.

In some embodiments, the above described kits further comprise a label instruction of administering the composition comprising acamprosate calcium or another pharmaceutically acceptable salt of acamprosate according to any dosage amount or dosing regimens described herein.

Methods of Treatment

In another aspect, provided are methods of treating a disease, disorder, symptom, or syndrome, such as a neuropsychiatric disorder, in a patient in need of such treatment comprising administering to said patient a composition or a unit dose of a composition described herein.

Exemplary diseases or disorders include tardive dyskinesia (TD), tardive dystonia, tardive akathisia, dystonia, blepharospasm, levodopa-induced dyskinesia (LID) in patients with Parkinson's disease, simple tics, Tourette Syndrome (TS), obsessive-compulsive disorder (OCD), post-traumatic stress disorder (PTSD), symptoms of schizophrenia, depression, bipolar disorder, autism spectrum disorders, autistic symptoms in Fragile X syndrome, alcoholism, tinnitus, and generalized anxiety disorder, and repetitive and stereotypic self-injurious behaviors (SIB) in persons with developmental disabilities such as biting, skin-picking, hitting oneself, and head-banging. In some embodiments, the method is for reducing anxiety and/or agitation in a patient receiving a neuroleptic, anxiety or antidepressant medication. In some embodiments, the method is for treating alcohol dependence.

In some embodiments the methods can include reducing the severity of or reducing or delaying the onset of a disease, disorder, symptom or syndrome. In some embodiments, the methods can include treating or selecting a particular patient, group or population of patient to receive treatment. For example, in some embodiments the methods can treat or select a patient in need of taking acamprosate or another medication described herein with food, without food, in a fed or in a fasted stated. The patient, group or population can be for example, one that is susceptible or needs to avoid GI side effects of acamprosate or the other medication, that needs to take a combination medication with or without food, and therefore desires to take the acamprosate or other medication in the same manner. In some embodiments the patient, group or population can be one that needs to minimize the number of pills taken per day or needs to take less than 2000 mg, 1500 mg or less of acamprosate daily with 2 or 3 total pills or less. In some cases, the patient, group or population can be those susceptible to non-compliance with an acamprosate or other treatment regimens or that need a regimen that requires fewer pills or side effects in order to encourage or facilitate compliance. In still other embodiments, the patient, group or population can include patients that need to avoid or delay the onset of side effects of a neuroleptic treatment, such as the onset of TD. In some other embodiments, the patient, group or population can include patients that experience anxiety or depression, and/or are taking a medication for anxiety or depression and need to treat a condition such as TD.

TD is a chronic disorder of the nervous system, characterized by involuntary, irregularly rhythmic movements most often involving the mouth, tongue, and facial muscles. Choreatic or dystonic movements of the extremities can be included, as can dystonic movements of the neck or trunk, and rocking movements of the trunk. TD with prominent limb and trunk movements eis especially disabling and difficult to treat. TD can be accompanied by tardive akathisia, an irresistible impulse to move which is often manifest as continual restless movements of the legs. Another potential accompaniment of TD is disruption of respiratory movements leading to irregular breathing and subjective shortness of breath—respiratory dyskinesia. Most cases of TD are caused by long-term use of neuroleptics (antipsychotic drugs); the remainder are caused by chronic use of dopamine blocking drugs such as metoclopramide or prochlorperazine that are given to relieve or to prevent nausea and vomiting or, in the case of metoclopramide, to treat diabetic gastroparesis. While most cases arise after months or years of exposure to the causative agent(s), there are numerous well-documented cases in which those drugs have induced TD after only a few weeks of exposure. Unlike many drug side effects, tardive dyskinesia usually worsens when the causative drug is discontinued, and the condition can persist for months, years, or even permanently afterwards. The prevalence of tardive dyskinesia with long-term treatment with first-generation antipsychotic drugs is over 25%, and even higher in elderly patients. While tardive dyskinesia occurs at a significantly lower rate with second-generation antipsychotic drugs, all of them except for clozapine are known to cause TD in some patients.

Additional diseases or disorders that can be treated with acamprosate or the composition described herein include dyskinetic movements in Rett's Syndrome, dyskinetic movements in the DiGeorge Syndrome, dyskinetic movements and dystonia in Wilson's disease and post-hypoxic myoclonus. It is contemplated that in some cases treatment of these disorders may require a higher acamprosate plasma concentration than that for treating TD. The ability of the composition described herein to provide high acamprosate plasma concentrations for at least a number of hours during a 24 hour period in combination with high tolerability for high dose acamprosate administered with or without food would enable the treatment of these disorders.

In some embodiments, the composition can be administered once, twice or three times daily. In some embodiments, the methods can include, for example, administering to a patient in need thereof a total daily dosage of acamprosate of from 500 mg to 4000 mg per day. In some embodiments, the methods may include, for example, administering to the patient acamprosate at a daily dosage of 1000 mg to 1500 mg, or 1300 mg to 1500 mg, or more, on a once-a-day schedule with or without food (in a fed or a fasted state). In some embodiments, the methods may include, for example, administering to the patient acamprosate at a daily dosage of 1000 mg to 1500 mg, or 1300 mg to 1500 mg, or more, on a twice-a-day schedule with or without food (fed or fasted). In some embodiments, the methods may include, for example, administering to the patient acamprosate at a daily dosage of 800 mg to 1500 mg (or any value or range there between, end points inclusive, such as 1300 mg to 1500 mg) once a day with or without food (fed or fasted). In some embodiments, the methods may include, for example, administering to the patient about 4000 mg of acamprosate per day. In some embodiments, the methods may include, for example, administering to the patient acamprosate in two tablets twice a day wherein each tablet comprises 800 mg to 1000 mg, of acamprosate. In some embodiments, the methods may include, for example, administering to the patient acamprosate in one tablet three times a day wherein each tablet comprises 1300 mg to 1400 mg of acamprosate. In some embodiments, the methods can include, for example, administering to the patient acamprosate in two tablets once a day, such as in the morning, and one tablet once a day, such as in the evening or about 10-14 hours before or after administration of the two tablets, wherein each tablet comprises 1300 mg to 1400 mg of acamprosate. The once or twice daily acamprosate administration respectively can be a dosage of 1000 mg, less than 1000 mg, more than 1000 mg, or equal to or less than 1400 mg, for example, in a dosage of 200 mg to 450 mg, or 350 mg to 900 mg, or 900 mg to 1400 mg. The administration of acamprosate is tolerated whether administered with or without food.

Without being limited thereto, when administered, the acamprosate can be administered as one, two or three units of a dosage form, for example, one, two or three pills or tablets. The single unit of a dosage form or the multiple units of a dosage form can have, for example, a total weight of up to 1500 mg, such as less than 1200 mg. For example, in some embodiments herein, the total unit dosage form weight can be between 400 and 1500 mg, between 500 and 1200 mg, between 600 and 1200 mg, or any value or sub range within those ranges. TABLE 1 below provides non-limiting dosing regimens.

In some embodiments, the patient is administered a composition or a unit dose of a composition described herein in a fed or fasted state, and the patient may choose to take each individual dose on each individual occasion in either the fed state or the fasting state. In some embodiments, the patient is administered a composition or a unit dose of a composition described herein in a fasted state. In some embodiments, the patient is administered a composition or a unit dose of a composition described herein in a fed state. In some embodiments, the methods specifically can exclude administration in the fasted or the fed state. In some embodiments, the patient is administered a composition or a unit dose of a composition described herein immediately prior to food intake (e.g., within 30 minutes or within 60 minutes of taking food), with food, or soon after food intake (e.g., within 30 minutes, within 60 minutes or within 2 hours of food intake). In some embodiments the patient is administered a composition or a unit dose of a composition described herein without food, for example, after an overnight fast, or not less than 30-60 minutes prior to a meal or not less than 1 hour, 2 hours, three hours after a meal, or more. In some embodiments, the patient is administered a composition or a unit dose of a composition described herein at least 1 hour, 2 hours, 3 hours, 4 hours, 5 hours, 6 hours, 7 hours, 8 hours, 9 hours, 10 hours, 11 hours, 12 hours or more after food intake, or any time there between. In some embodiments, the patient is administered a composition or a unit dose of a composition described herein at least 30 minutes before food intake, at least 1 hour, 2 hours, 3 hours, 4 hours, 5 hours, 6 hours, 7 hours, 8 hours, 9 hours, 10 hours, 11 hours, 12 hours or more before food intake, or any time there between.

In some embodiments, acamprosate is administered once or twice daily, for example, to achieve the total daily dosage, and the administered acamprosate can be in a composition that is formulated to release at least 50% of the acamprosate over a 2-8 hour period or any sub value or sub range there between. In some aspects, at least 50% is released within the first 4 hours. In some aspects, at least 90% is released from the composition within 8 hours.

In some embodiments, when the composition is given TID, it can be taken for example with food for one or two doses and without food for one or two doses.—This is made feasible by the fed-fasting equivalence. In some embodiments, when a patient is already taking other medications doses of the acamprosate formulation provided herein can be taken in conjunction with other medications, favoring compliance. It is noted that most patients with neuropsychiatric disorders will be on other medications. In some embodiments, a patient tolerates the formulation provided herein better with food—or better without food and the formulation can be taken in any suitable manner without any concern of the difference in therapeutic effect.

Pharmacokinetics and Compositions and Methods Related Thereto

Some embodiments herein are related to methods and compositions where the pharmacokinetics (PK) of acamprosate are altered.

It was surprisingly found that the compositions described herein can exhibit substantially the same PK profile when administered to a patient in a fed state or in a fasted state. The effect of food to reduce acamprosate absorption did not occur. For example, a formulation comprising 800 mg of acamprosate exhibited substantially the same PK profile in the fed and fasted states. The compositions according to at least some embodiments can release acamprosate by diffusion, substantially proportionally to the square root of time in vitro, and can maintain their integrity in the GI tract for several hours when administered in a fed state or in the fasted state. Also, more than 50% of the drug can be released within, for example, about 3-5 hours. Still further, unexpectedly and surprisingly it was found that even through the amount of acamprosate is much higher than two Campral® tablets each comprising 333 mg of acamprosate calcium, the formulation comprising 800 mg or more of acamprosate calcium was well-tolerated in humans in both in a fed state and in a fasted state, with only one subject (8.3% of a 12-subject sample) reporting any GI side effect (diarrhea) in the fasted state, and no subject reporting any GI side effect in the fed state. The data indicate that the compositions of the instant technology (e.g., those comprising 800 mg to 1500 mg acamprosate) are more tolerable than Campral® from the GI standpoint, especially because patients will have the option of taking the drug with food (in a fed state) if they have GI side effects in the fasted state, as there are no food effects on PK.

Immediate-release (IR) acamprosate (which is equivalent to acamprosate solution because acamprosate is immediately and completely soluble in gastric juice) has twice the bioavailability of enteric-coated acamprosate (Saivin S et al., Clinical Pharmacokinetics of Acamprosate, Clinical Pharmacokinetics Vol. 35, Number 5, November 1998, pp. 331-345, which is incorporated herein by reference in its entirety). However, IR acamprosate has a PK profile characterized by a relatively high and early Cmax and a relatively rapid decline in plasma concentration after Cmax is attained, without wishing to be bound by any theories, it is contemplated that the therapeutic efficacy of acamprosate probably is based on maintaining the acamprosate plasma level above a threshold concentration for a minimum number of hours per day. For example, efficacy might require a residence time of 6 hours above 200 ng/mL for a single dose. The dosage of IR acamprosate needed to produce this residence time would be associated with a higher Cmax with than the dose of the formulation described herein needed to produce this residence time. IR acamprosate would thus have two reasons to produce more GI side effects than the formulation described herein—a higher local concentration of acamprosate in the stomach, and a higher maximum plasma concentration.

Campral® tablets have a Tmax of over 8 hours and a dose-normalized Cmax well below that of the present formulations; their PK curve is relatively flat. Adding to the shape of the PK curve consideration of the food effect on absorption, to consistently attain an above-threshold residence time (for the acamprosate plasma level) of six or eight hours a day using Campral® will usually require attaining a level near or above the threshold for 24 hours a day. Considering this point and the food effect one can conclude that the total daily dosage of the acamprosate formulations described herein required for therapeutic efficacy for a given condition may be substantially lower than the total daily dosage of Campral® that would be required for the same therapeutic efficacy. Therefore the formulations described herein may be efficacious for neuropsychiatric indications at dosages and on dosing regimens that are better tolerated and more conducive to long-term treatment adherence than the ones that would be necessary using Campral®.

For the just-noted reasons the sustained release formulations described herein may be efficacious at total daily doses of less than 1 gram per day, and when they are and these formulations could be given on a twice-daily schedule, and even on a once-daily schedule, depending on the threshold plasma level and daily time above that level required for efficacy in a given patient. Depending on the indication, the minimum number of hours a day the acamprosate plasma level that must be above a threshold to attain therapeutic efficacy might be four, six, or eight hours, or some other number of hours. However it is very unlikely that the plasma level for therapeutic efficacy would need to be maintained continuously over 24 hours for any indication, because the mechanism of action of acamprosate is via inducing the alteration of glutamate receptor composition and conformation, and not via the ongoing occupancy of glutamate receptor sites. The model system studied was based on sustained release over eight hours. In some embodiments, it is evident that sustained release over six hours or sustained release over four hours can be satisfactory for therapeutic advantage, depending on the time and concentration thresholds for efficacy in particular patient populations and for particular indications. The following TABLE 1 illustrates example dosing regimens.

TABLE 1

| Total daily dosage | Dosage per tablet | Dosing schedule |
| --- | --- | --- |
| 1.5 grams | 1.5 grams | 1 tablet once a day |
| 3 grams | 1.5 grams | 1 tablet twice a day |
| 4.5 grams | 1.5 grams | 2 tablets in the morning and 1 tablet in the evening |
| 1 gram | 1 gram | 1 tablet once a day |
| 2 grams | 1 gram | 1 tablet twice a day |
| 4 grams | 1 gram | 2 tablets twice a day |
| 800 mg | 800 mg | 1 tablet once a day |
| 1.6 grams | 800 mg | 1 tablet twice a day |
| 3.2 gram | 800 mg | 2 tablets twice a day |
| 400 mg | 400 mg | 1 tablet once a day |
| 800 mg | 400 mg | 1 tablet twice a day |
| 1.6 grams | 400 mg | 2 tablets twice a day |

Enteric-coated acamprosate is only half as bioavailable as IR acamprosate and has a lower maximum concentration ($C_{max}$) and longer time to peak concentration ($T_{max}$) than IR acamprosate. The sustained release acamprosate formulation provided herein has an even greater therapeutic advantage over enteric-coated acamprosate than over IR acamprosate. Furthermore, the steady-state concentration in the plasma when enteric-coated acamprosate is given three times a day is approached slowly over 5-7 days, with the plasma level of acamprosate during the first several days of administration below the eventual steady-state plasma level. By contrast, a sustained release formulation of acamprosate given in the fed or fasted state according to embodiments described herein that provides sustained delivery of acamprosate where a single dose can reach the plasma level of acamprosate attained only after several days on the enteric-coated version, and it can maintain that level for a number of hours sufficient for efficacy although in some cases the level is not maintained for the entire 24-hour period. In some embodiments, it is believed that the therapeutic efficacy of an acamprosate formulation depends upon its producing plasma levels above a threshold for a minimum number of hours per 24-hour day—but not all 24 hours necessarily. Not wishing to be bound by any theory, it is contemplated that this is because the mechanism of action of acamprosate in the brain is based on synthesis of proteins that persist for many hours after they are synthesized. Further, clinical observations of Campral® treatment suggest that unevenly distributed TID dosing can give better therapeutic results than evenly distributed TID dosing, which may produce a low, flat PK curve. That at steady state one would be either above threshold all the time or below it all the time. Thus a high daily dosage of Campral® is needed in order that the steady state is above the threshold. While the IR acamprosate would provide high plasma level for at least a number of hours, there would be a tolerability concern related to high local concentrations in the stomach and a high $C_{max}$ in the plasma. The novel SR formulations described herein provide for several hours above a potential therapeutic threshold after each dose—without attaining the high $C_{max}$ that would be needed to get the same residence time with an IR preparation, and without having the high local gastric concentration of drug one would have with an IR preparation.

Thus, consistent with the human case set forth in EXAMPLE 1 that evidences that there is a therapeutic threshold that needs to be exceeded for significantly less than 24 hours, for example, six or eight hours per 24 hours, the dosing of 400 mg of sustained release acamprosate twice a day, or possibly 800 mg once a day, can be effective in some embodiments. This supports efficacy in some cases for the sustained release formulation at a total daily dose of less than 1000 mg per day—less than the previously recognized therapeutic range and not explained by mere bioequivalence with some dose in the previously recognized therapeutic range. Because this lower dose of the SR preparation would not have a greater AUC than the same dose of Campral®, its efficacy is not expected from the prior art, which does not explicitly include alternate formulations of acamprosate that produce the same concentrations of acamprosate in blood and/or brain as those produced by doses of 1 gram to 2.6 grams of Campral®, the only formulation available at the time the prior art was published.

Further, it should be understood that according to some embodiments the sub gram, twice or once a day regimens (e.g., 400 mg twice a day or 800 mg once a day regimens) of sustained release acamprosate do not give equivalent concentrations in the plasma to those produced by enteric-coated acamprosate given in a higher total daily dose on a three times daily schedule. The latter would give—after 5-7 days—a stable level of acamprosate, whereas the sustained release regimens described herein can produce a fluctuating level of acamprosate that might be below the steady state level for enteric-coated acamprosate, at some times of the day. Thus, the sustained release formulations given at less than 1 gram per day would not be bio-equivalent to the enteric-coated formulation given at dosages of 1 gram to 2.6 grams on a three times a day schedule, and in fact, in some embodiments, it would usually have a 24-hour AUC in less than that produced by Campral® given on a typical TID schedule (e.g., 333 mg TID). For these reasons the use of sustained release acamprosate at a daily dose of less than 1 gram per day given on a once-daily or twice-daily basis in the fed or fasted state is not suggested by the prior art, and its (expected) efficacy for TD (and for other neuropsychiatric disorders) is a novel and unexpected discovery.

The sustained release acamprosate formulations (e.g., tablets) according to some embodiments herein can thus be of size such that the total tablet or pill is easy to swallow. For example, the specifically described formulations herein, in particular, 400 mg sustained release acamprosate tablets, 800 mg, and even up to 1500 mg sustained release acamprosate tablets are small enough to be easily swallowed. They thus make possible reasonably-sized fixed-dose combination tablets comprising sustained release acamprosate and another drug that is given in a substantially lower dosage than the sustained release acamprosate, typically at a dosage of less than 200 mg per day.

In some embodiments, provided is a way to administer a therapeutic dosage of acamprosate in one (relatively) small dose that only has to be taken once or twice daily. The smaller dosage form also can have ancillary benefits. First of all, the smaller dosage can lead to lesser side-effects. It also can lead to improved patient compliance due to being taken fewer times each day, for example, once daily. Additionally, smaller dosage forms allow for more convenient co-administration of acamprosate with other drugs, for example as part of a single dosage form or as separate dosage forms.

In some embodiments, administration of a composition or a unit dose of a composition described herein provides a plasma concentration having an area under curve (AUC) at 8 hours after administration that is at least 33% of the AUC at 48 hours after administration.

In some embodiments, administration of a composition or a unit dose of a composition described herein to a patient provides substantially the same PK profile in said patient whether it is administered in a fed state or in a fasted state. In some embodiments, the pharmacokinetic profiles in a fed state and in a fasted state are considered bioequivalent by a regulatory agency, such as the U.S. Food and Drug Administration (e.g. 80-125% of a reference product). In some embodiments, administration of the composition or unit dose to the patient results in a 90% confidence interval (CI) for acamprosate plasma $C_{max}$ in the fed state being 90 to 110% of the $C_{max}$ in the fasted state. In some embodiments, administration of the composition or unit dose to the patient results in a 95% CI for acamprosate plasma $C_{max}$ in the fed state being 90 to 110% of the $C_{max}$ in the fasted state. In some embodiments, administration of the composition or unit dose to the patient results in a 90% CI for acamprosate plasma $T_{max}$ in the fed state being 90 to 110% of the $T_{max}$ in the fasted state. In some embodiments, administration of the composition or unit dose to the patient results in a 95% CI for acamprosate plasma $T_{max}$ in the fed state being 90 to 110% of the $T_{max}$ in the fasted state. In some embodiments, administration of the composition or unit dose to the patient results in a 90% CI for acamprosate plasma AUC in the fed state being 90 to 110% of the AUC in the fasted state. In some embodiments, administration of the composition or unit dose to the patient results in a 95% CI for acamprosate plasma AUC in the fed stated being 90 to 110% of the AUC in the fasted state. In some embodiments, administration of the composition or unit dose to the patient results in two or more of the above. In some embodiments, administration of the composition to the patient results in all of the above.

In some embodiments, the methods can include, for example, administering an acamprosate dosage form once or twice per day to a patient in a fed state wherein the dosage form comprises up to 4 grams of acamprosate for example, and a total dosage of from 1 gram to 4 grams of acamprosate, per day. In some embodiments, such a dosage form is retained upon administration in a fed state in the stomach of the patient for at least 4 hours. In some embodiments, the methods can include comprises administering an acamprosate dosage form once or twice per day to a patient in a fasted state wherein the dosage form comprises up to 4 grams of acamprosate, for example, from 1 gram to 4 grams of acamprosate, per day, which dosage form upon administration is retained in the stomach of the patient for no more than one hour when administered in a fasted state. In some embodiments, each unit of the dosage form comprises about 800 mg of acamprosate, and is administered once, twice or three times daily, and when administered once or twice daily, one unit or two units of the dosage form can be administered. In some embodiments, each unit of the dosage form comprises about 1300 mg of acamprosate, and is administered once, twice or three times daily, and when administered once or twice daily, one unit or two units of the dosage form can be administered. In some embodiments, the method is for treating tardive dyskinesia.

In some embodiments, provided are compositions for and methods of maintaining an in vivo steady-state acamprosate plasma concentration for at least 4-8 hours, preferably about 6 hours, out of a 24 hour period at or above a minimum level needed for therapeutic efficacy for treating a neuropsychiatric or other medical condition in a patient in need thereof. The method may include, for example, administering to the patient a dosage of a pharmaceutically acceptable salt of acamprosate, wherein the dosage form comprises up to 1.5 grams of acamprosate formulated in a polymer matrix that releases acamprosate by diffusion, and the dosage is administered either once daily or twice daily. In some embodiments, the dosage form may include less than 1 gram of acamprosate.

It surprisingly has been discovered that in some embodiments acamprosate treatment can be efficacious even though the acamprosate concentration does not exceed the threshold for the entire 24 hour period or even though the concentration or levels of acamprosate are very inconsistent (not at steady levels) during a given period of time such as a 24 hour period. The methods described herein where several hours of exposure—typically between 4 and 8 hours—to an adequate level of acamprosate can produce therapeutic effects on CNS function lasting for hours after the level of acamprosate falls—and often for the remainder of a 24 hour day. Thus, a single dose of an acamprosate composition designed to release the drug over a 4-8 hour period, such as those described herein, can be sufficient to give a 24 hour therapeutic effect.

It has been discovered that the shape of the PK curve and not just the AUC can make a difference to efficacy. Specifically, having a plasma concentration above a threshold for several hours per day (e.g., 4-8 hours) may be more efficacious than maintaining a concentration just below that threshold for 24 hours a day. In a simulated dog model of a sustained release it was shown that sustained presentation of acamprosate over eight hours yielded a significantly longer residence time above a threshold concentration than immediate release of the same dosage, even when there was not a significant difference in the AUC. In this model, the drug conserved by avoiding a high single dose and high $C_{max}$ was distributed across several hours, giving a several hour period in which the plasma concentration of acamprosate was higher than the plasma concentration after administration of a single dose of the immediate release version.

Immediate release formulation was found to release acamprosate in a strict dose linearity of AUC and $C_{max}$ with oral dosing between 333 and 2664 mg, albeit with 6 subjects. Saivin S, Hulot T, Chabac S, et al.: Clinical pharmacokinetics of acamprosate. Clinical Pharmacokinetics 35(5): 331-345, 1998.

Further, clinical observations of TD cases were made showing that enteric coated acamprosate (Campral®) given three times daily had greater efficacy lower daily dosage when the daily dosage was divided unevenly among the three doses, even when the total number of pills administered per 24 hours in less in the uneven schedule than the normal schedule. Not wishing to be limited by any theory, it is noted that the therapeutic action of acamprosate in TD is based on its effects on glutamate transmission. These effects are not based on direct interaction of acamprosate with glutamate receptors, but rather on downstream effects of acamprosate modulation at other sites on the neuron. Reilly M T, Lobo I A, McCracken L M, et al.: Effects of acamprosate on neuronal receptors and ion channels expressed in *Xenopus Oocytes*. Alcoholism Clinical and Experimental Research 32(2): 188-196, 2008. These downstream effects are based in part on modulation of protein synthesis, a mechanism implying the potential for persistence of effect after the drug is no longer present at a threshold level for clinical efficacy.

In some embodiments, the pharmaceutically acceptable salt of acamprosate is formulated in a polymer matrix that releases, by diffusion in vitro, approximately 50% of the acamprosate within 2 hours and releases at least 80% of the acamprosate within 4-6 hours.

In some embodiments, the steady-state in vivo acamprosate plasma concentration is maintained at or above a threshold for therapeutic efficacy for at least 6 hours out of a 24 hour period, wherein the therapeutic threshold is about 100 ng/mL, 150 ng/mL, 200 ng/mL, 250 ng/mL, 300 ng/mL, 350 ng/mL, 400 ng/mL, 450 ng/mL, or 500 ng/mL, or any ranges between any two of the numbers (end points inclusive).

In some embodiments a formulation of acamprosate which can provide a higher $C_{max}$ and shorter $T_{max}$ than Campral® for an equal dose will be efficacious at a lower total daily dose, where sustained absorption leads to attaining a therapeutic threshold for a sufficient number of hours a day. In some embodiments, the therapeutic threshold is a plasma level of not higher than 1000 ng/mL and generally not less than 100 ng/mL (or any value or range there between, the endpoints inclusive). In some embodiments, the therapeutic threshold is a plasma level of not higher than 500 ng/mL and generally not less than 200 ng/mL. In some embodiments, a plasma level of at least 150 ng/mL or at least 200 ng/mL is attained for at least 6 hours, 7 hours, or 8 hours, or any ranges between any two of the values, end points inclusive. In some embodiments, a plasma level of at least 100 ng/mL or at least 200 ng/mL is attained within one hour after administration. In some embodiments, $T_{max}$ is attained in 1 to 5 hours or 2 to 5 hours.

In another aspect, provided herein is a composition comprising acamprosate, having one or more of the following in vitro dissolution properties:
1) remaining substantially intact for at least 4-12 hours at pH 1.0 or at pH 4.5 or a pH between about 1.0 and about 4.5, (e.g., the composition stays firm or very firm and elastic or can be picked up with slight resistance and does not disintegrate; however, the composition can swell to a bigger size, such as some or all dimensions are from about 100% to 200% of the original),
2) dimensions of the composition are within 80% to 200% of the original dimensions),
3) releasing acamprosate by diffusion at a rate substantially proportional to the square root of time, (e.g., the average release rate of acamprosate from the formulation is within 80% to 120% of the rate that is proportional to the square root of time),
4) releasing more than 50% of acamprosate within 4 hours and approximately 80% of acamprosate at 6 hours,
5) having substantially equivalent in vitro acamprosate releasing profiles at pH 1.0 and pH 4.5,
6) comprising at least 400 mg of acamprosate, and
7) having a minimum length along at least one axis of 10 mm and a maximum length on at least one axis of 30 mm, such as each dimension is independently selected from 12 mm, 15 mm, 20 mm, 25 mm, or any value or sub-range there between.

In some embodiments, the in vitro release profile at pH 1.0 can be determined by placing a composition described herein in a vessel filled with a 1M HCl aqueous solution, for example, by following the procedure described in EXAMPLE 4. In some embodiments, the in vitro release profile at pH 4.5 can be determined by placing a composition described herein in a vessel filled with an aqueous acetate solution, for example, by following the procedure described in EXAMPLE 4.

In some embodiments, the composition can include, for example, acamprosate calcium or another pharmaceutically acceptable salt of acamprosate, and a high molecular weight polymer, including for example, those capable of forming a hydrogel matrix when contacting water, such as a PAA or carbomer described herein, polyox (polyethylene oxide), HPMC (hydroxypropylmethylcellulose), PVA (polyvinyl alcohol), PA (polyacrylic acid) and its derivatives, Xanthan gum, metolose (cellulose derivative), and poly(2-hydroxymethyl)methacrylate. In some embodiments, the polymer is able to provide a sufficient hardness and low friability over a wide range of compression forces and form a matrix (e.g., a hydrogel matrix) when contacting water such that the composition retains its integrity in a solution and in the GI tract. In some embodiments, the polymer is present in the composition at from about 1% to about 25% of the total weight of the composition, such as about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% of the total weight of the composition, or any value or ranges between any two of the numbers (end points inclusive). The compositions can include a dosage of acamprosate as set forth herein, for example. The compositions can release the acamprosate according to the profiles described herein, and/or can provide a pK profile (one or more of the parameters herein) that is within 80%-120% of the profiles of one or more of the formulations of Example 3. Thus, one or more of the excipients described above can be substituted for or included with the carbomers described herein to provide formulations with substantially the same properties. Such formulations also can be taken in a fed or fasted stated, with or without food as desired, and can be combined with the other medications as described herein.

In some embodiments, provided herein is a composition comprising acamprosate, wherein when administered to a human in a fed state the composition is retained in the stomach for at least 3-4 hours.

In some embodiments, provided herein is a composition comprising acamprosate, wherein when administered to a human in a fasted state the composition is retained in the stomach for no more than three hours, such as no more than two hours, or no more than one hour.

In some embodiments, provided herein is a composition comprising acamprosate, wherein when administered to a human in a fed state or in a fasted state the composition is substantially intact when it reaches the colon.

In some embodiments provided herein is a composition that is retained in the stomach for more than 3-4 hours (such as at least 5 hours, 6 hours, 7 hours, 8 hours, 9 hours, 10 hours, 11 hours, or 12 hours, or any range within any two of the values, end points inclusive) when given in the fed state, thus releasing most of acamprosate in the stomach and thus exposing most of the released acamprosate to the entire small intestinal surface, thereby maximizing absorption via diffusion. In some embodiments, the composition is in the jejunum within 3 hours (or 2.5 hours, 2.25 hours, 2 hours, 1.5 hours, 1 hour, or 30 minutes, or any range within any two of the values, end points inclusive) when administered to a patient in a fasted state, thus most of the drug is released more distally, and does not compete with food for absorption. In some embodiments, the location of the composition does not substantially affect the release rate of acamprosate. Without being bound to any theory, it is believed that these surprising behaviors of the composition provides balance of many different factors influencing release and absorption of acamprosate, such that the AUC and $C_{max}$ of plasma levels are substantially the same when the composition is administered to the subject in the fed state and when the composition is administered to the subject the fasted state.

In some embodiments, the composition comprises 700 mg to 1500 mg acamprosate in each unit that is formulated so that the composition is retained in the stomach for at least 4 hours when administered to a patient in a fed state. In some embodiments, the composition comprises 700 mg to 1500 mg acamprosate in each unit that is formulated so that the composition is retained in the stomach for no more than 3 hours or no more than 1 hour when administered to a patient in a fasted state.

In some embodiments, provided herewith is a composition comprising a pharmaceutically acceptable salt of acamprosate, such as acamprosate calcium, wherein when administered to a human releases acamprosate at substantially the same rate in vivo as it does in vitro.

In another aspect, provided herein is a composition comprising a pharmaceutically acceptable salt of acamprosate, such as acamprosate calcium, wherein when administered to a human said composition produces a plasma concentration of acamprosate characterized by one or more of the following:
1) The 8-hour AUC is on average at least one-third of the 48-hour AUC;

2) The 12-hour AUC is on average at least one-half of the 48-hour AUC.
3) The average $C_{max}$ is less than about 500 ng/ml after a single unit of the composition comprising up to about 800 mg of a pharmaceutically acceptable salt of acamprosate, such as acamprosate calcium, is administered,
4) The average $C_{max}$ is less than about 750 ng/ml after a single unit of the composition comprising up to about 1200 mg of a pharmaceutically acceptable salt of acamprosate, such as acamprosate calcium, is administered,
5) The average AUC and $C_{max}$ are substantially the same when the composition is administered to humans in the fed state and when the composition is administered to humans in the fasted state.

In some embodiments, the composition comprises acamprosate calcium or another pharmaceutically acceptable salt of acamprosate and a high molecular weight polymer, such as a PAA or carbomer described herein, polyox (polyethylene oxide), HPMC (hydroxypropylmethylcellulose), PVA (polyvinyl alcohol), PA (polyacrylic acid) and its derivatives, Xanthan gum, metolose (cellulose derivative), and poly(2-hydroxy-methyl)methacrylate. In some embodiments, the polymer is able to provide a sufficient hardness and low friability over a wide range of compression forces and form a hydrogel matrix when contacting water such that the composition retains its integrity in a solution and in the GI tract. In some embodiments, the polymer is present in the composition at from about 1% to about 25% of the total weight of the composition, such as about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% of the total weight of the composition, or any value or ranges between any two of the numbers (end points inclusive). The compositions can include a dosage of acamprosate as set forth herein, for example. The compositions can release the acamprosate according to the profiles described herein, and/or can provide a pK profile (one or more of the parameters herein) that is within 80%-120% of the profiles of one or more of the formulations of Example 3. Thus, one or more of the excipients described above can be substituted for or included with the carbomers described herein to provide formulations with substantially the same properties. Such formulations also can be taken in a fed or fasted stated, with or without food as desired, and can be combined with the other medications as described herein.

In some embodiments, provided herein is a composition comprising a pharmaceutically acceptable salt of acamprosate, such as acamprosate calcium, wherein when administered to a human the formulation is well-tolerated whether administered with or without food. In some embodiments, the composition is well tolerated even when administered at a dosage of up to 4 grams per day. In some embodiments, a 3 to 4 gram daily dose can be administered in two tablets twice a day (BID) wherein each tablet comprises 750 to 1000 mg of acamprosate. In some embodiments, a 4 gram dose can be administered in one tablet three times a day (TID) wherein each tablet comprises 1300 mg to 1400 mg of acamprosate. In some embodiments, a 2.6 gram dose can be administered in two tablets once a day, such as in the morning, or two tablets once a day, such as in the evening, wherein each tablet comprises 1300 of acamprosate.

In some embodiments, provided herein are methods of treating a neuropsychiatric disorder that can include for example administering a composition comprising up to 1500 mg of a pharmaceutically acceptable salt of acamprosate, such as acamprosate calcium, once or twice a day. In some embodiments, the composition comprising less than 1 gram, such as 800 mg of a pharmaceutically acceptable salt of acamprosate, such as acamprosate calcium, is administered once a day. It is surprising that 800 mg of acamprosate in the composition administered once a day would be effective in treating a neuropsychiatric disorder as 800 mg is lower than the lowest dose of Campral® ever reported to be or claimed to be therapeutically effective for any condition. For example, the currently-marketed enteric-coated acamprosate calcium tablets must be given on a three times daily schedule in doses of 2 grams or more per day to be efficacious in treating alcoholism, and many patients require more than 2 grams or more to get relief of symptoms. Similarly, when used to treat TD and other neuropsychiatric disorders, Campral® has been used by one of the inventors on an open-label basis at dosages ranging from 1 gram to 3.6 grams per day (3 to 11 tablets daily) on a thrice-daily schedule. The average minimal dose for obtaining an optimal response in treating TD with Campral® on an open-label basis has been 3 grams daily. Case reports of the use of Campral® for other neuropsychiatric indications such as tinnitus or autism have always used no less than 333 mg TID.

Some embodiments relate to methods for reducing or eliminating gastrointestinal side effects associated with acamprosate treatment, which method comprises administering a acamprosate composition described herein. It was found that even though the amount of acamprosate calcium in an 800 mg tablet of a formulation described herein is significantly higher than that in two Campral® tablets each comprising 333 mg of acamprosate calcium, the formulation comprising 800 mg or more of acamprosate calcium was well-tolerated in humans in both in a fed state and in a fasted state, with only one subject (8.3% of 12 subjects reporting any GI side effect (diarrhea) in the fasted state, and no subjects reporting diarrhea in the fed state, or any other GI side effect in either the fed or the fasting state. In some embodiments, the method comprises administering to a patient in need acamprosate treatment a total daily dosage of acamprosate of less than 1000 mg, wherein the acamprosate is administered once or twice daily to achieve the total daily dosage, and the administered acamprosate is in a composition that is formulated to release at least 50% of the acamprosate over a 4-8 hour period. In some aspects, at least 50% is released within the first 4 hours. In some aspects, at least 90% is released from the composition within 8 hours. The side effect to be reduced or eliminated can be, for example, nausea, diarrhea, dyspepsia and/or vomiting. In some embodiments, the method comprises administering an acamprosate composition described herein in a fed state. In some embodiments, the method comprises administering an acamprosate composition described herein in a fasting state in which the formulation is retained in the stomach for no more than 1 hour.

In some embodiments the side effect is reduced by administering a composition described herein, in particular a sustained release version of acamprosate, as compared with the immediate-release version, since the maximum concentration of the drug in the gastric juice or in the intestine, and the maximum concentration in the blood, will be lower than with the immediate release version.

The most common side effects of acamprosate that can be reduced or eliminated are gastrointestinal symptoms—including nausea, vomiting, diarrhea, and dyspepsia. For patients with alcoholism these side effects often lead to noncompliance, and in turn to decreased effectiveness of treatment. For patients with TD, who often are so distressed by their movements that they will adhere to effective treatment despite side effects, the gastrointestinal side effects make treatment unpleasant, or limit the acamprosate dose to one that does not completely relieve their involuntary movements. For all patient groups taking multiple pills three times daily is inconvenient and burdensome. The reduced side effects, and/or reduced dosage and administration frequency made possible by the compositions described herein will improve treatment compliance.

Combinations and Related Methods of Treatment

In some embodiments, the methods described herein further comprises administering the formulations of acamprosate with one or more other medications, such as first-generation neuroleptic (antipsychotic) drugs, second generation neuroleptic drugs, selective serotonin reuptake inhibitors (SSRIs), serotonin norepinephrine reuptake inhibitors (SNRIs), or the anti-nausea drug metoclopramide, such as those described herein. The other medication can be administered with acamprosate in a fixed dose form or in separate dosage forms simultaneously or sequentially, such as at a different time, on the same or different dosing schedule, as long as patient is being treated with both medication. For example, the decreased dosage amount and frequency of dosing made possible by the formulations described herein makes it feasible to formulate fixed-dose combinations of acamprosate and other medications, such as first-generation neuroleptic drugs. The fixed dose combinations with first-generation neuroleptics, for example, can provide effective treatment of psychosis with a lesser risk of metabolic side effects than seen with second-generation neuroleptic drugs, a lesser risk of tardive dyskinesia than seen with first generation neuroleptic drugs given alone, and with, unexpectedly, increased relief of mental symptoms compared with first-generation neuroleptic drugs given alone.

Some embodiments relate to combinations of from 500 mg to 4 grams, or 100 mg to less than 1 gram (e.g., 800 mg) of a pharmaceutically acceptable salt of acamprosate with a drug from a second class, for example, where the second drug is given in a dose ranging from half of the lower end of its usual dosage range to the upper end of its dosage range. The combination pill may be given either once or twice a day to treat a neuropsychiatric disorder, for example.

The fixed dose compositions comprising a first or second generation neuroleptic combined with a formulation of acamprosate described herein can be used to treat any of the disorders treated with, for example, neuroleptic drugs or metoclopramide, including schizophrenia, schizoaffective disorder, bipolar disorder, major depression, delusional disorder, organic psychoses, delirious agitation, or nausea and vomiting. They can be given for this purpose on a once-daily or twice-daily schedule (or more if desired), typically with a single pill or tablet given each time. They can provide for a given dosage of neuroleptic, equal or greater benefit for the neuropsychiatric disorder or symptoms being treated, and can offer greater relief of anxiety and agitation when these are among the symptoms. Compared with the same dose of a first-generation neuroleptic given without acamprosate, these combinations entail a lower risk of tardive dyskinesia and other tardive movement disorders, and they will cause movement disorder of lesser severity, if they cause one at all. In contrast with second-generation neuroleptics of equal therapeutic efficacy, these combinations can carry a lesser risk of significant metabolic disturbances including weight gain, glucose intolerance, and increased risk of atherosclerotic cardiovascular disease.

Some embodiments relate to methods of reducing the risk or delaying the onset of tardive dyskinesia comprising administering to a patient in need thereof a combination as described herein. Some embodiments relate to methods of continuing neuroleptic treatment in a patient who already has tardive dyskinesia but requires continued neuroleptic therapy for a chronic mental disorder; treatment with the combination of acamprosate and the neuroleptic reduces the severity of the TD while providing equal or greater benefit in treating the mental disorder.

In the case of acamprosate combined with a neuroleptic, the combination may reduce the risk or delay the onset of tardive dyskinesia (TD) associated with giving the neuroleptic drug. Also, unexpectedly, the combination has additional benefits for the patient's mental status, such as decreased anxiety and/or agitation (as shown in Example 1 and 2 below). If the patient has pre-existing TD associated with cognitive impairment the acamprosate may also provide an improvement in cognition. The action of acamprosate to treat—and consequentially to prevent the manifestation of—tardive dyskinesia, combined with the additional benefit of improving some mental symptoms—makes higher-potency and first-generation neuroleptic drugs more attractive when they are given in combination with acamprosate. At present the first-generation, high-potency neuroleptic drugs are avoided because they are more likely than second-generation neuroleptic drugs to produce tardive dyskinesia. However, those drugs are no less efficacious in treating psychosis than the second-generation drugs (with the sole exception of clozapine), and second-generation drugs usually are more expensive, and have serious metabolic effects with potentially life-threatening consequences. It is rational to combine even second-generation neuroleptics with acamprosate, because those drugs still carry some risk of TD, and the additional psychiatric benefit can still apply. TABLES 11 and 12 below show non-limiting examples of the dose ranges for the neuroleptic drugs and the sustained-release acamprosate formulation to be used in fixed dose combinations. It should be noted that the potential therapeutic benefits of combining acamprosate with a neuroleptic drug are not limited to combinations that comprise a sustained-release formulation of acamprosate. They are expected with any acamprosate formulation that is tolerated by the patient at a dosage adequate for therapeutic effect. The minimum efficacious dosage will be lower with the sustained-release formulations of acamprosate described herein than with Campral®, and the sustained-release formulations described herein may also have a higher maximum tolerable dosage than either IR acamprosate or Campral®.

In another aspect, provided herein are compositions and methods that combine acamprosate, in any formulation, such as for example immediate release (IR), sustained release (SR), or enteric-coated, etc., with neuroleptic medications, such as those described herein. Examples such medications include, without limitation, perphenazine, lamotrigine, quetiapine, others described herein and any other neuroleptic medication.

Some embodiments relate to methods of treating a patient suffering from a disorder requiring treatment with a neuroleptic drug. The methods can include selecting a subset of such patients also in need of reducing psychiatric conditions such as anxiety or depression.

EXAMPLES

Example 1

Case 1: A 56-year old woman had long-standing tardive dyskinesia induced by treatment of schizoaffective disorder with a variety of neuroleptics and mood stabilizers. Her TD was characterized by side to side movements of the jaw, grimacing movements, rocking of the trunk, and continual involuntary kicking, leg-crossing, and twisting movements of her legs and feet. At the time she presented for treatment of her TD she was treated for her mental illness with lamotrigine and quetiapine, a second-generation neuroleptic. She was started on Campral® 666 mg three times a day, with partial relief of symptoms. When Campral® was increased to 999 mg three times a day she had complete relief of her TD. After two months free of symptoms of TD she switched from quetiapine to perphenazine, a first-generation neuroleptic; her TD symptoms did not return. After the switch to perphenazine the patient had less daytime sedation than with quetiapine, stopped gaining weight, and had fewer symptoms of anxiety and depression.

After additional weeks free of TD symptoms she discontinued the Campral®. Her TD symptoms returned, as did feelings of anxiety and agitation that had not been present while she was on the combination of Campral® and perphenazine.

She resumed Campral®, again finding that 666 mg three times a day did not give her complete relief, but 999 mg three times a day did. On this dose she again got relief of anxiety and agitation.

To test the hypothesis that the efficacy of Campral® was related to adequate time above a threshold plasma level the patient was asked to try taking 1332 mg once a day and 666 mg for her other two doses. On this dose she continued to be free of involuntary movements of TD, but did have significant GI side effects of diarrhea and abdominal cramps.

The results showed efficacy of Campral® for TD at a lower total daily dose, when instead of distributing the dose evenly, a larger proportion of the dose was given at one time. This demonstrates that the use of Campral® at a concentration above a therapeutic threshold value for a sufficient number of hours per 24-hour day (e.g., 6-14 hours, preferably about 8) can be sufficient to give a 24-hour therapeutic effect. The case also shows that individual doses of over 1 gram of Campral® at one time may be poorly tolerated.

Example 2

CASE 2: A 34-year old man had been treated with Campral® for several years for TD due to exposure to several neuroleptics for schizoaffective disorder. He was currently treated with lamotrigine and quetiapine for his mental illness, and was taking Campral® 1332 mg+999 mg+1332 mg on a three times daily basis. This dose of Campral® completely relieved his involuntary movements of TD—the latter including involuntary movements of the cheeks and mouth, rocking movements of the trunk, and twisting movements of the both upper and lower extremities. 999 mg three times a day did not give full relief from his involuntary movements. To test the therapeutic threshold hypothesis the patient was asked to try 1332 mg of acamprosate once a day in the morning. On this dose he was free of movements in the morning and early afternoon but movements returned in the evening. When he added a second dose of 1332 mg in the late afternoon—approximately 8 to ours after his first dose—he obtained complete relief of symptoms. He noted that when he got relief of his involuntary movements he also had less anxiety and agitation than when the movements were present.

Both of these cases support two hypotheses: 1) That the treatment response to acamprosate calcium in TD (and presumably in other neuropsychiatric disorders characterized by recurrent unwanted stereotypic symptoms) is related to the amount of time the acamprosate plasma level is above a specific threshold, and not on the AUC of the PK curve. This is so because in both cases the patient did better on regimens that had a lower total daily dose of acamprosate calcium but utilized either a higher single dose on one occasion or changed the spacing of doses so as to provide a higher plasma concentration of acamprosate for several hours a day than would be seen with the baseline regimen at steady state. This is unexpected, because it has not been known heretofore that lower total daily doses of acamprosate calcium could work better than higher ones if dosages were divided unevenly or spaced differently during the 24-hour day so as to attain a higher $C_{max}$ at steady state. (2) That the combination of acamprosate calcium with a neuroleptic can provide relief of anxiety and agitation associated with psychosis and TD. This is unexpected, because acamprosate calcium by itself does not have anti-anxiety effects.

In a dog study of simulated sustained release of acamprosate it was shown that through sustained release a higher residence time above a threshold can be attained than by giving the same dose all at once. Combining the results from the dog study with the implications of the reported human cases we contemplate that acamprosate delivered by a sustained release system can relieve symptoms of TD and other neuropsychiatric disorders given once or twice a day. A single 800 mg dose of sustained-release acamprosate calcium can produce a residence time of four hours above a potential single-dose therapeutic threshold of 200 ng/mL; 666 mg of Campral® did not do this even in the fasting state and, and would not do so at a dosage of even 1332 mg either, given the dose-proportionality of its pharmacokinetics. Thus it appears that a total daily dose of less than one gram of sustained release acamprosate, given on a twice a day basis, or perhaps even on a once a day basis, could be adequate to treat TD in the case examples. Therefore in some cases— probably the majority of cases—of TD cases the minimum effective daily dose of acamprosate delivered by a sustained release system could be less than 1 gram—the minimum of the range of efficacious dosages reported heretofore for the enteric-coated formulation (Campral®). It should be noted further that experience to date with the enteric-coated tablets (Campral®) has never shown them to fully relieve the symptoms of TD at doses of 1 gram, whereas here in some embodiments daily doses of less than 1 gram can offer complete symptom relief and not just a detectable therapeutic effect.

Example 3

Sustained Release Formulations of Acamprosate Calcium

The tablets swell when they come in contact with gastric juices; they are retained in the stomach for several hours if they are administered in the fed state (e.g., at the conclusion of a meal). If administered in the fasted state they rapidly (30 minutes-2 hours) move to the small intestine. The formulation has been manufactured as 400 mg and 800 mg tablets. These are standard round bi-convex white tablets with beveled edges. Both tablet strengths are spray coated with Opadry® II White (Colorcon, Inc.) for ease of swallowing. Purified water is the vehicle for the Opadry; it evaporates during the coating process. The total weight of the coating is between 2% and 4% of the pre-coating weight.

Table 2 shows the ingredients of two tablets (400 mg tablet and 800 mg tablet) having Carbopol 974P® prior to coating:

TABLE 2

| Ingredient | Function | Amount (mg) in S.R. 400 mg tablet | Amount (mg) in S.R. 800 mg tablet |
|---|---|---|---|
| Acamprosate calcium | Active ingredient | 400 | 800 |
| Povidone K-90 | Binder | 50 | 50 |
| Microcrystalline cellulose | Diluent | 320 | 100 |
| Colloidal silicon dioxide | Glidant | 10 | 10 |
| Citric acid | Acidulant | 60 | 0 |
| Carbopol 974P | Polymer | 60 | 60 |
| Carboxymethylcellulose | Polymer | 40 | 40 |
| Starcap 1500 | Disintegrant | 40 | 40 |
| Talc powder | Filler | 10 | 10 |
| Magnesium stearate | Lubricant | 10 | 10 |
| Total prior to coating | | 1000 | 1120 |

Tablets comprising Carbopol 974P® and 300 mg and 600 mg acamprosate calcium were also prepared. The Pharmacokinetics of these tablets were found to be dose proportional.

Example 4

Sustained Release Formulations of Acamprosate Calcium

Table 3A shows ingredients of the granules for preparing tablets comprising 800 mg of acamprosate and Carbopol® 971P. Tables 3B and 3C show the ingredients of two 800 mg tablets having varying amount of Carbopol® 971P:

TABLE 3A

Granulation: Lot 111113

| Material | mg | gram |
|---|---|---|
| Acamprosate calcium | 800 | 800 |
| PVP K90 | 50 | 50 |
| Avicel PH102 | 100 | 100 |
| Cabosil | 10 | 10 |
| Total | 960 | 960 |
| Water | | 120 gms |

TABLE 3B

Blend: Lot 111213-A

| | mg | gram |
|---|---|---|
| Granules, 111113 | 960 | 48 |
| Carbopol 971 P | 60 | 3 |
| CMC 7HF | 40 | 2 |
| Starcap 1500 | 40 | 2 |
| Talc | 10 | 0.5 |
| MGST | 10 | 0.5 |
| Total | 1120 | 56 |

TABLE 3C

Blend: Lot 111213-B

| | mg | gram |
|---|---|---|
| Granules, 111113 | 960 | 48 |
| Carbopol 971 P | 80 | 4 |
| CMC 7HF | 20 | 1 |
| Starcap 1500 | 40 | 2 |
| Talc | 10 | 0.5 |
| MGST | 10 | 0.5 |
| Total | 1120 | 56 |

Example 5

Dissolution Profiles of the 400 mg and 800 mg Sustained Release Acamprosate Tablets of Example 3

400 mg or 800 mg tablets were dissolved in either acetate solution (pH 4.5) or 1M HCl (pH 1.0). The percentage of the active ingredient released into the solution was determined at 1, 2, 4, 6, 8, and 10 hours. Each release profile was assessed in six different test vessels. Tables 4-7 display the results, demonstrating that release is approximately linear with the square root of time. The fourth column in each table displays the amounts of drug that would be released if the release were exactly proportional to the square root of time, with a specified coefficient that ranges from 0.27 to 0.3.

TABLE 4

Release of Acamprosate from 400 mg Tablets from EXAMPLE 3 (Sustained release Acamprosate formulation) in Acetate Solution (pH 4.5) - (n = 6)

| Time (hours) | SQRT Time | Mean % of Total Drug Released | 27% * SQRT Time | S.D. of % of Total Drug Released | Minimum % Released | Maximum % Released |
|---|---|---|---|---|---|---|
| 0 | 0.0000 | 0.00 | 0.00 | 0.00 | 0 | 0 |
| 1 | 1.0000 | 24.09 | 27.00 | 1.40 | 23 | 27 |
| 2 | 1.4142 | 36.09 | 38.18 | 2.34 | 34 | 40 |
| 4 | 2.0000 | 54.39 | 54.00 | 4.02 | 49 | 60 |
| 6 | 2.4495 | 70.11 | 66.14 | 4.15 | 64 | 76 |
| 10 | 3.1623 | 87.67 | 85.38 | 4.21 | 83 | 95 |
| 12 | 3.4641 | 92.31 | 93.53 | 4.38 | 87 | 99 |

TABLE 5

Release of Acamprosate from 400 mg Tablets of EXAMPLE 3 (Sustained Release Acamprosate formulation) in 0.1N HCl (pH 1.0) - (n = 6)

| Time (hours) | SQRT Time | Mean % of Total Drug Released | 27% * SQRT Time | S.D. of % of Total Drug Released | Minimum % Released | Maximum % Released |
|---|---|---|---|---|---|---|
| 0 | 0.0000 | 0.00 | 0.00 | 0.00 | 0 | 0 |
| 1 | 1.0000 | 31.60 | 27.00 | 1.58 | 24 | 27 |
| 2 | 1.4142 | 44.83 | 38.18 | 3.20 | 36 | 41 |
| 4 | 2.0000 | 63.20 | 54.00 | 4.42 | 56 | 62 |
| 6 | 2.4495 | 75.27 | 66.14 | 5.42 | 69 | 74 |
| 10 | 3.1623 | 91.31 | 85.38 | 3.59 | 85 | 91 |
| 12 | 3.4641 | 95.99 | 93.53 | 2.96 | 90 | 96 |

TABLE 6

Release of Acamprosate from 800 mg Tablets of EXAMPLE 3 (sustained release Acamprosate formulation) in Acetate Solution (pH 4.5) - (n = 6)

| Time | SQRT Time | Mean % of Total Drug Released | 30% * SQRT Time | S.D. of % of Total Drug Released | Minimum % Released | Maximum % Released |
|---|---|---|---|---|---|---|
| 0 | 0.0000 | 0.00 | 0.00 | 0.00 | 0 | 0 |
| 1 | 1.0000 | 31.60 | 30.00 | 1.58 | 29 | 34 |
| 2 | 1.4142 | 44.83 | 42.43 | 3.20 | 42 | 51 |
| 4 | 2.0000 | 63.20 | 60.00 | 4.42 | 58 | 64 |
| 6 | 2.4495 | 75.27 | 73.48 | 5.42 | 70 | 84 |
| 10 | 3.1623 | 91.31 | 94.87 | 3.59 | 87 | 97 |
| 12 | 3.4641 | 95.99 | 100.00 | 2.96 | 91 | 100 |

TABLE 7

Release of Acamprosate from 800 mg Tablets of EXAMPLE 3 (Sustained release Acamprosate formulation) in 0.1N HCl (pH 1.0) - (n = 6)

| Time (hours) | SQRT Time | Mean % of Total Drug Released | 29% * SQRT Time | S.D. of % of Total Drug Released | Minimum % Released | Maximum % Released |
|---|---|---|---|---|---|---|
| 0 | 0.0000 | 0.00 | 0.00 | 0.00 | 0 | 0 |
| 1 | 1.0000 | 28.11 | 29.00 | 1.21 | 26 | 29 |
| 2 | 1.4142 | 41.56 | 41.01 | 1.77 | 40 | 44 |
| 4 | 2.0000 | 61.48 | 58.00 | 2.38 | 57 | 63 |
| 6 | 2.4495 | 75.41 | 71.04 | 1.61 | 73 | 77 |
| 10 | 3.1623 | 92.24 | 91.71 | 0.55 | 92 | 93 |
| 12 | 3.4641 | 96.62 | 100.00 | 0.65 | 96 | 97 |

Example 6

Dissolution Profiles of the 400 mg and 800 mg Sustained Release Acamprosate Tablets of Example 3

Tables 8-10 display the results of contacting the tablets described in Example 4 with either acetate solution (pH 4.5) or 1M HCl (pH 1.0). The results in Tables 9 and 10 are also illustrated in FIGS. 1-4, showing that the dissolution profile is substantially proportional to the square root of time.

TABLE 8

Swell test of 800 mg Tablets of EXAMPLE 4

| | Lot No: 111213-A | | Lot No: 111213-B | |
|---|---|---|---|---|
| Medium: | HCl | Acetate | HCl | Acetate |
| Initial Length (cm) | 1.28 | 1.28 | 1.28 | 1.28 |
| Length 5 min (cm) | 1.4 | 1.4 | 1.45 | 1.45 |
| Length 30 min (cm) | 1.5 | 1.5 | 1.55 | 1.5 |
| Length 1 hr (cm) | 1.55 | 1.52 | 1.6 | 1.52 |
| Length 2 hr (cm) | 1.65 | 1.55 | 1.7 | 1.55 |
| Length 6 hr (cm) | 1.9 | 1.65 | 1.95 | 1.7 |
| % Swelling | 148% | 129% | 152% | 133% |
| Firmness Rating | 4.5 | 4 | 4.8 | 4 |
| Initial Thick (cm) | 0.77 | 0.78 | 0.78 | 0.78 |
| Final Thick (cm) | 1.5 | 1.3 | 1.55 | 1.3 |
| % Swelling | 195% | 167% | 199% | 167% |

Observations:
1) The Swelling results are comparable to SNC-102 tablets.
2) No erosion is seen.
3) % Swelling is more in lot 111213-B compared to lot 111213-A
4) The swollen tablets are intact and firm for 6 hours during the swelling test.

Firmness Rating System:
1. Shapeless after 6 hours in acid
2. Loosely retains shape, very soft
3. Retains shape, but offers no resistance
4. Can be picked up, slight resistance
5. Very firm and elastic

TABLE 9

Dissolution Profile of 800 mg Tablets of EXAMPLE 4 in HCl Solution

| Time (hours) | SQ of Time | HCL 111213-A | HCL 111213-B |
|---|---|---|---|
| 0 | 0 | 0 | 0 |
| 1 | 1 | 30.21 | 29.97 |
| 2 | 1.4142 | 42.22 | 44.21 |
| 4 | 2 | 58.63 | 62.71 |
| 6 | 2.4495 | 70.15 | 74.75 |
| 10 | 3.1623 | 84.94 | 89.04 |
| 12 | 3.4641 | 88.14 | 92.79 |

TABLE 10

Dissolution Profile of 800 mg Tablets of EXAMPLE 4 in Acetate Solution

| Time (hours) | 111213-A | 111213-B |
|---|---|---|
| 0 | 0 | 0 |
| 1 | 36.41 | 34.24 |
| 2 | 49.75 | 47.42 |
| 4 | 68.76 | 64.53 |
| 6 | 80.72 | 77.94 |
| 10 | 93.94 | 92.93 |
| 12 | 96.34 | 95.68 |

Example 7

Combination of Reformulated Acamprosate with First-Generation Neuroleptics

First-generation neuroleptic (antipsychotic drugs) have been used for over 50 years in the treatment of schizophrenia and other psychotic disorders, as well as in the treatment and prevention of nausea and vomiting. The first of these drugs to be introduced to the market was chlorpromazine; others include thioridazine, perphenazine, trifluoperazine, haloperidol, fluphenazine, loxapine, and molindone. Their common feature is that they are all dopamine antagonists at both D2 and D3 dopamine receptors; each has its own distinctive set of effects on receptors for other neurotransmitters. One of the major drawbacks of these drugs is their propensity to cause movement disorders. With acute administration they can cause movement disorders including Parkinsonism (tremor, rigidity, bradykinesia and gait instability) as well as dystonia, dyskinesia, and akathisia. Given chronically they can cause chronic movement disorders that persist even if the drug is stopped and may even be permanent. These disorders include tardive dyskinesia (TD), tardive dystonia, and tardive akathisia. The incidence of TD and other tardive movement disorders with long-term use of first-generation neuroleptics exceeds 25%, with an even higher rate in elderly patients. In part because of the very high risk of TD, a second generation of neuroleptics was developed that has a lower risk of causing TD and related movement disorders with chronic administration. These drugs include risperidone, quetiapine, clozapine, olanzapine, and aripiprazole. The incidence of TD with these drugs is less than 5%, but all are associated with metabolic side effects of sufficient severity to affect life expectancy. These side effects include weight gain, glucose intolerance, and disturbances in lipid metabolism. With the exception of clozapine the second-generation neuroleptics are not more effective in treating schizophrenia and other psychotic disorders. Clozapine, while more effective as treatment for severe mental illness, has additional serious medical side effects including a significant incidence of agranulocytosis that requires frequent monitoring of patients' white blood cell counts as a requirement for using the drug. The first generation neuroleptics, especially the higher-potency ones, have a much lower incidence of metabolic side effects than the second-generation neuroleptics, and some first generation neuroleptics, e.g., molindone, do not have them at all.

If first generation neuroleptics could be given without a high risk of causing or exacerbating tardive dyskinesia they would be preferable to second-generation neuroleptics for treating most patients with psychotic disorders as they would lack the troublesome metabolic side effects of the latter. (While many patients would have some degree of acute extrapyramidal side effects from the first-generation antipsychotic drugs, these often can be managed by either reducing the dose, switching to a less potent agent, or adding an antiparkinsonian drug. Tolerance can develop to acute extrapyramidal side effects as well. TD and related potentially-irreversible tardive movement disorders remain the single greatest drawback to the use of the first generation antipsychotic drugs.) Some embodiments herein relate to utilizing fixed-dose combinations of first-generation neuroleptics with new formulations of acamprosate designed for delayed release via a sustained release delivery system. Such combinations would not have been practical heretofore because of the high doses of acamprosate needed to treat TD if the existing enteric-coated tablet formulation is used. Given the compliance issues common among psychiatric patients a regimen of more than two pills daily would risk diminished effectiveness. If significantly more than a gram of acamprosate were needed to treat TD the combination of an effective dose of acamprosate for TD with an effective dose of a first-generation neuroleptic would need to be divided among at least three pills, as a dose of enteric-coated acamprosate significantly larger than 500 mg in a single pill might require that pill to be unpleasantly large, even without the addition of a second drug. The actual dosage of enteric-coated acamprosate needed to treat TD might in fact be much higher—more than 3 grams in some cases. On the other hand, if the needed dose of different formulation of acamprosate needed were less than one gram, treatment effective for both psychosis and TD could be delivered by one or two combination pills. Such is the case with the instant formulations described herein that provide for sub-gram dosages and formulations of acamprosate.

While it is not known whether co-administration of acamprosate with a neuroleptic drug will completely prevent the emergence of TD in all cases, it can be expected that it will diminish the severity of any TD that does develop, and that it acamprosate might suppress symptoms of TD if it continues to be given, even if some dyskinesia could appear if the acamprosate were discontinued. In the two case examples, patients with established TD and a mental disorder took acamprosate together with a neuroleptic and had complete relief of their TD symptoms. Those patients would also be free of TD symptoms if they took the same combination without having TD at baseline. The incidence of TD will be lower if a first generation neuroleptic is co-administered with a dose of acamprosate that would be efficacious to treat established TD in the majority of patients. If TD did develop in some patients the severity would necessarily be less than if acamprosate were not given.

Some embodiments therefore relate to among other things the following two technologies: (1) Compositions containing a dose of a first generation neuroleptic adequate to treat a psychotic disorder and a dose of acamprosate adequate to treat or prevent tardive dyskinesia, including compositions in which the doses of the neuroleptic and the acamprosate are combined in a single pill, and compositions in which the doses are divided into multiple units delivered concurrently, e.g., one tablet of each drug in a single blister pack; and (2) The use of such compositions to treat one or more of schizophrenia, bipolar disorder, schizoaffective disorder, depression with psychotic features, delusional disorder, other psychotic conditions, the symptoms of hallucinations and delusions. The compositions in some aspects further can treat or prevent the symptoms of nausea and vomiting that often accompany the use of such medications. In the described technologies the use may be in patients with or without established TD. The preferred formulation of acamprosate would be a sustained release formulation of the type described herein, though compositions utilizing other formulations of acamprosate could be effective for the purpose if the dose of acamprosate were adequate.

It is surprising and unexpected that in some embodiments doses of acamprosate lower than the heretofore-described dosing range for treating TD can be effectively used, even though such lower doses may not have the same PK profiles as the enteric-coated pills utilized in previously-described treatment of TD—and such lower doses can in some embodiments produce a 24-hour AUC lower than that produced by similarly efficacious doses of enteric-coated acamprosate. Further, we note the unexpected finding that patients with TD and mental disorders who received acamprosate together with a neuroleptic showed an unexpected improvement in anxiety and agitation, even though acamprosate alone does not affect these symptoms.

It should be evident that to attain therapeutic advantages described herein from the pharmacokinetics described, which are different in critical ways both from IR acamprosate and from the marketed formulation of acamprosate, the specific technology for formulating the sustained release delivery system for acamprosate does not matter as long as that system that can delivers substantially equivalent PK curves in the fed and the fasting state. This will follow from the formulation having substantially equivalent in vitro release kinetics, and being a formulation that will release its active ingredient in the same way regardless of its location in the GI tract.

TABLE 11 lists first-generation neuroleptic drugs and range of daily dosages at which they are usually prescribed. Some embodiments herein relate to tablets or capsules that implement one of the sustained release technologies in Table 12 delivering a dosage of acamprosate between 200 and 1000 mg, together with a dose of one of the drugs described in TABLE 11 at one of the dosages specified in that table or a dosage of one-half of the minimum dose in the table below, and up to the maximum dose or any value there between. As an example, a tablet might comprise 4 mg of perphenazine together with 250 mg of acamprosate formulated in a sustained release preparation, with the perphenazine surrounding a core of acamprosate, or alternatively mixed with the acamprosate throughout the tablet.

TABLE 11

First Generation Neuroleptics and Metoclopramide:
Daily Dosages and Doses for Fixed-Dose Combination Pills.

| Drug | Daily Dose Range (mg) | Example Single Pill Dosages (mg) in Combination with Acamprosate |
|---|---|---|
| Thioridazine | 10-200 | 10, 25, 50, 100 |
| Chlorpromazine | 25-200 | 25, 50, 100 |
| Thiothixene | 2-50 | 2, 5, 10, 25 |
| Trifluoperazine | 5-50 | 5, 10, 25 |
| Fluphenazine | 2-50 | 2, 5, 10, 25 |
| Haloperidol | 0.5-50 | 0.5, 1, 2, 5, 10, 20 |
| Perphenazine | 2-32 | 2, 4, 8, 16 |
| Loxapine | 10-100 | 1, 10, 25, 50 |
| Molindone | 10-200 | 10, 25, 50, 100 |
| Metoclopramide | 5-60 | 5, 10, 15 |

Example 8

Combination of Acamprosate with Second-Generation Neuroleptics

The dose of sustained release acamprosate can be between 200 mg and 1000 mg. Regarding the neuroleptic dosage, the principle is that the minimum dose is approximately one-half of the smallest currently marketed dose of the drug. Examples of the dosage ranges of some non-limiting examples of first-generation neuroleptics are given in TABLE 11. Examples of dosage ranges for some second-generation neuroleptics are shown in the following TABLE 12. For example, the dosage for the neuroleptic can range from one-half of the minimum dose in the table below, and up to the maximum dose, or any value there between:

TABLE 12

| Neuroleptic | Minimum Dose | Maximum Dose |
|---|---|---|
| aripiprazole | 1 mg | 30 mg |
| asenapine | 1 mg | 10 mg |
| iloperidone | 1 mg | 24 mg |
| lurasidone | 10 mg | 120 mg |
| olanzapine | 1 mg | 20 mg |
| paliperidone | 1 mg | 12 mg |
| quetiapine | 12.5 mg | 400 mg |

TABLE 12-continued

| Neuroleptic | Minimum Dose | Maximum Dose |
|---|---|---|
| risperidone | 0.25 mg | 4 mg |
| ziprasidone | 10 mg | 80 mg |

Example 9

Combination of Acamprosate with SSRI and SSRI Antidepressants

SSRIs and SNRIs are efficacious in OCD and PTSD, both conditions that also can respond to treatment with acamprosate. Also, SSRIs and SNRIs are used to treat depressive and anxiety disorders in which recurrent, unwanted, stereotyped thoughts, perceptions, and behavior may be part of the syndrome. Since acamprosate and the serotonin reuptake inhibitors have different mechanisms of action, their therapeutic effects on these disorders can be synergistic. A published study describes augmentation of the benefits of an SSRI for generalized anxiety by adding Campral® at a dose of 333 mg TID. (Reference)). The fact that sustained release acamprosate can be efficacious at a daily dose of less than one gram a day, on a once or twice daily schedule, makes fixed-dose combinations of sustained release acamprosate with an SSRI or SNRI feasible.

The dose of sustained-release acamprosate can be between 200 mg and 800 mg. Some embodiments relate to combinations where the minimum dose is approximately one-half of the smallest currently-marketed dose of the drug, for example one-half of the minimum dose in the table below, and up to the maximum dose or any value there between.

TABLE 13

| SSRI or SNRI | Minimum Dose | Maximum Dose |
|---|---|---|
| Citalopram | 5 mg | 40 mg |
| Desvenlafaxine | 25 mg | 100 mg |
| Duloxetine | 5 mg | 60 mg |
| Escitalopram | 2.5 mg | 20 mg |
| Fluoxetine | 5 mg | 40 mg |
| Fluvoxamine | 12.5 mg | 100 mg |
| Milnacipran | 6.25 | 100 mg |
| Paroxetine | 5 mg | 40 mg |
| Sertraline | 12.5 mg | 200 mg |
| Venlafaxine | 12.5 mg | 150 mg |

Example 10

The pharmacokinetic properties of the specific sustained release preparation of acamprosate described in EXAMPLE 3 were tested in human subjects (healthy male volunteers of age over 18 years) in single-center Phase I studies. Specific issues addressed in the studies were: (1) Dose proportionality of pharmacokinetics of the EXAMPLE 3 formulation; (2) Comparison of acamprosate described in EXAMPLE 3 with IR acamprosate (acamprosate solution); (3) Comparison of the EXAMPLE 3 formulation with the marketed formulation of enteric-coated acamprosate tablets (Campral®) in the fed state and the fasting state; and (4) Comparison of the pharmacokinetics of the EXAMPLE 3 formulation in the fed and the fasting state. The main findings of the studies show that the EXAMPLE 3 formulation has pharmacokinetic properties that make it therapeutically superior both to Campral® and to IR acamprosate, and, that the EXAMPLE 3 formulation has the remarkable, unexpected and therapeutically relevant property that its pharmacokinetics are equivalent in the fed and the fasting state.

Example 11

In the first study, subjects received, 30 minutes after a standard high-fat meal, a single dose of 400 mg of sustained release acamprosate (EXAMPLE 3), of 800 mg of sustained release acamprosate (EXAMPLE 3), or of 666 mg of enteric-coated acamprosate (Campral®). Plasma concentrations of acamprosate were determined at within 1 hour (pre-dose) of dosing and 1, 2, 3, 4, 5, 6, 8, 10, 12, 18, 24, 36 and 48 hours after dosing and pharmacokinetic parameters were calculated.

11 subjects were dosed with 400 mg sustained release acamprosate formulation, 11 subjects were dosed with 800 mg sustained release acamprosate formulation, in tablets, and 12 were subjects dosed with Campral® 666 mg. Results are presented in TABLES 14-15 below.

Dose Proportionality:

SR acamprosate was readily absorbed following a single oral dose of sustained release acamprosate formulations, both 400 and 800 mg doses. Median $T_{max}$ occurred at 4.00 hours post dose for both the 400 mg and 800 mg doses; the range of $T_{max}$ was 3.00-5.00 hours for the 400 mg dose and 3.00-6.00 hours for the 800 mg dose. Mean $C_{max}$ was 299 ng/mL for the 800 mg dose, which was essentially twice the mean value of 148 ng/mL for the 400 mg dose. Mean $AUC_{0-t}$ and $AUC_{0-\infty}$ for the 800 mg dose of sustained release acamprosate were 4440 and 4600 h·ng/mL, respectively. Mean $AUC_{0-t}$ and $AUC_{0-\infty}$ for the 400 mg dose of sustained release acamprosate were 2220 and 2240 h·ng/mL, respectively. The $AUC_{0-t}$ for the 800 mg dose was exactly twice that for the 400 mg dose, and the $AUC_{0-\infty}$ for the 800 mg dose was minimally greater than that for the 400 mg dose. The data for $C_{max}$, $AUC_{0-t}$, and $AUC_{0-\infty}$ indicate dose proportionality of PK parameters for single doses of sustained release acamprosate formulations.

The mean apparent terminal half-life of the 800 mg dose of sustained release acamprosate formulation and the 400 mg dose of sustained release acamprosate formulation was 12.6 and 12.7, respectively, indicating that the half-life of acamprosate was essentially independent of dose strengths of sustained release acamprosate formulation. This observation permits inferences about the likely steady-state residence times above the therapeutic threshold when the sustained-release formulation is dosed long-term on a QD ore BID basis.

TABLE 14

Dose Proportionality of Pharmacokinetics of SR Acamprosate Administered in the Fed State to Healthy Male Volunteers

| Treatment | 800 mg sustained release | | 400 mg sustained release | |
|---|---|---|---|---|
| Parameters | N | Mean ± SD | N | Mean ± SD |
| $C_{max}$, ng/mL | 11 | 299 ± 67.2 | 11 | 148 ± 60.4 |
| $T_{max}$, h[a] | 11 | 4.00 (3.00-5.00) | 11 | 4.00 (3.00-6.00) |
| $AUC_{0-48}$, h·ng/mL | 11 | 4440 ± 1090 | 11 | 2220 ± 724 |
| $AUC_{0-\infty}$, h·ng/mL[b] | 8 | 4600 ± 1170 | 5 | 2240 ± 665 |
| $t_{1/2}$, h | 8 | 12.6 ± 4.42 | 5 | 12.7 ± 5.75 |

[a]median (range) is reported for this parameter.
[b]AUC to infinity and the T½ could not be calculated in all 11 subjects because the terminal part of the PK curve could not be fitted using standard software in all of the subjects.

Figure 5:
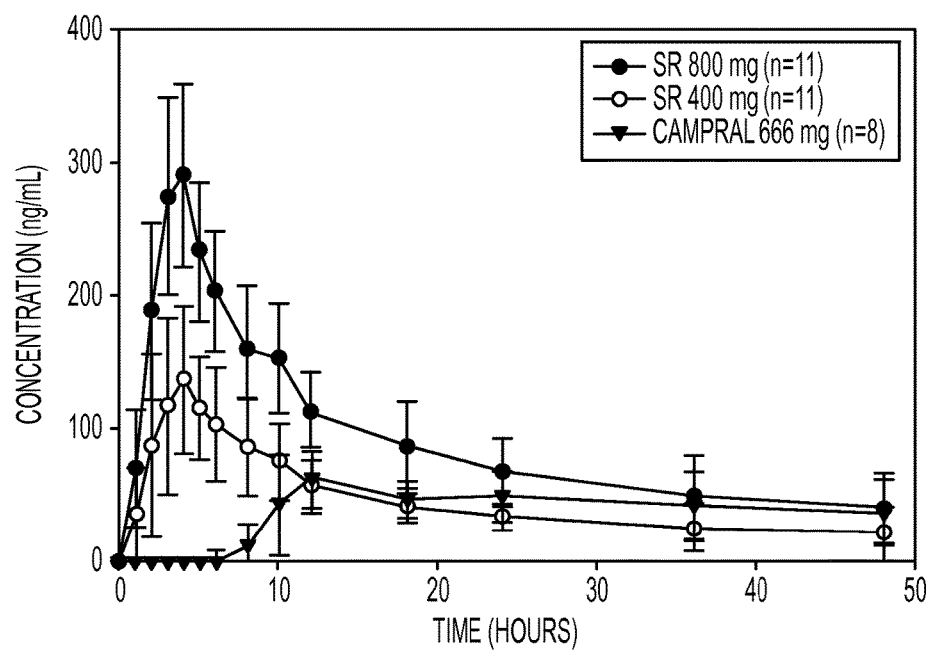
FIG. 5 shows the plasma concentrations of Campral® and 800 mg sustained release formulation and 400 mg sustained release formulation of Example 3 when administered in the fed state (30 minutes after a high-fat meal).

The comparison of dose-normalized PK parameters among Campral® and the two sustained-release formulations, all three administered in the fed state (30 minutes after a high-fat meal) are presented below presented below and in FIG. 5. The data indicated rate and extent of absorption of acamprosate of 800 mg sustained release formulation and 400 mg sustained release formulation, as reflected by systemic exposure $C_{max}$ and $AUC_{0-48}$ values, were dramatically faster and higher than those with Campral® 666 mg under fed conditions. For example, in the fed state 800 mg of Campral would not even attain a Cmax of 100 ng/mL, let alone attain a residence time of several hours above 200 ng/mL. The discussion of food effect in the Campral® package insert would not prepare one for a more than three-fold difference in Cmax between Campral and the SR version in the fed state. The data in Table 15 imply that even four Campral tablets—1132 mg, would not reliably provide a peak plasma level over 200 ng/mL if the drug were taken in the fed state.

TABLE 15

Comparison of Dose-Normalized Pharmacokinetic Parameters Between Campral ® and Sustained-Release Acamprosate Calcium Administered to Healthy Male Volunteers in the Fed State

| Formulation | N | GM (95% CI)a | | | |
|---|---|---|---|---|---|
| | | $DNC_{max}$* (ng/mL) | DNAUC0-48* (hr · ng/mL) | DNAUC0-∞* (hr · ng/mL) | $T_{max}$** (hr) |
| 800 mg sustained release | 11 | 244 (207, 288) | 3607 (3191, 4076) | NR | 4.00 (3.00-5.00) |
| 400 mg sustained release | 11 | 229 (177, 297) | 3570 (2783, 4581) | NR | 4.00 (3.00-6.00) |
| Campral ® 666 mg | 8 | 73 (56, 96) | 1684 (1199, 2366) | NR | 12.00 (10.00-24.00) |

| Comparison | GMR [90% CI] | | |
|---|---|---|---|
| | $C_{max}$*** | AUC0-48*** | AUC0-∞*** |
| 800 mg sustained release vs. Campral ® 666 mg | 333.11 [269.40,411.90] | 214.14 [169.27,270.90] | NR |
| 400 mg sustained release vs. Campral ® 666 mg | 312.74 [240.48,406.72] | 212.00 [167.04,269.06] | NR |

TABLE 15-continued

Comparison of Dose-Normalized Pharmacokinetic Parameters Between Campral ® and Sustained-Release Acamprosate Calcium Administered to Healthy Male Volunteers in the Fed State

| | | | |
|---|---|---|---|
| 400 mg sustained release vs. 800 mg sustained release | 93.88 [77.67, 113.48] | 99.00 [84.66,115.76] | NR | aGM = Geometric least-squares mean; CI = Confidence interval;
*Back-transformed least squares mean and confidence interval from mixed effects model performed on natural log-transformed values. $C_{max}$, $AUC_{0-48}$ and $AUC_{0-\infty}$ of acamprosate were normalized to 666 mg. $DNC_{max}$ is the dose normalized $C_{max}$; $DNAUC_{0-48}$ is the dose normalized $AUC_{0-48}$; $DNAUC_{0-\infty}$ is the dose normalized $AUC_{0-\infty}$. All parameters were normalized to a dose of 800 mg.
**Median (Minimum, Maximum).
***GMR = Geometric least-squares mean ratio between Treatments.
NR: Not reportable since most subjects' $AUC_{0-\infty}$ at Treatment C (Campral ® 666 mg) were not estimable.
Treatment A: 800 mg sustained release acamprosate formulation (Synchroneuron Inc.);
Treatment B: 400 mg sustained release formulation (Synchroneuron Inc.);
Treatment C: Campral ® 666 mg (as two 333 mg tablets) (Forest Pharmaceuticals, Inc.)

Under fed conditions, the relative bioavailability of the 00 mg sustained-release formulation and of the 400 mg sustained release formulation compared to Campral 666® mg were 214% and 212%, respectively. The relative Cmax were 333% and 313%, respectively.

Single doses of 800 mg and 400 mg EXAMPLE 3 sustained release formulations were safe and well tolerated when administered 14 days apart in healthy adult males. No gastrointestinal adverse events were reported, in keeping with clinical experience that GI side effects of acamprosate are less when the medication is taken with food.

Example 12

Figure 6:
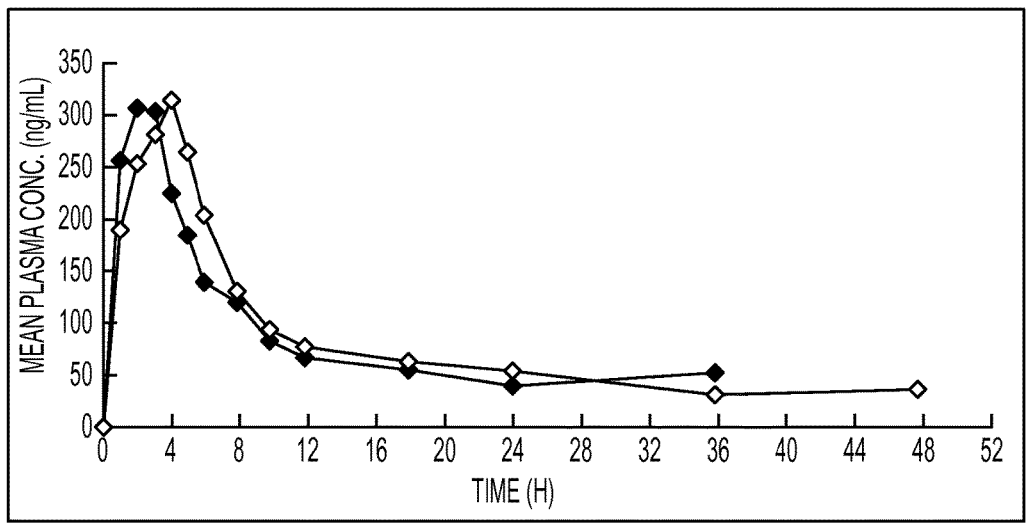
FIG. 6 shows the arithmetic mean acamprosate plasma concentration-time profiles following administration of oral doses of 800 mg sustained release tablet to humans under fed and fasting conditions—linear scale.
Figure 7:
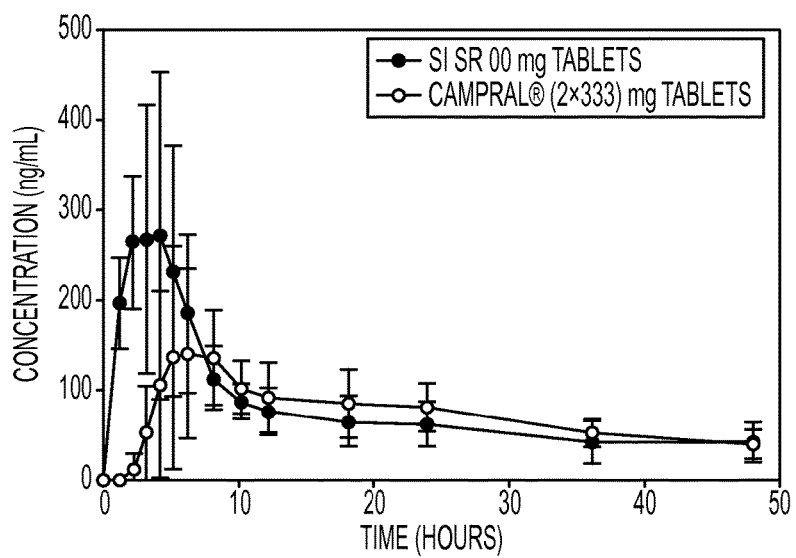
FIG. 7 shows the arithmetic mean acamprosate plasma concentration-time profiles following administration of oral doses of 800 mg sustained release tablets and Campral® 666 mg tablets under fasting conditions—linear scale.

In another study subjects received 800 mg of sustained release acamprosate formulation of EXAMPLE 3 in the fasted state, 800 mg of sustained release acamprosate formulation of EXAMPLE 3 in the fed state. For comparison, another study was conducted where subjects received 666 mg of enteric-coated acamprosate (Campral®) in the fasted state or 666 mg of enteric-coated acamprosate (Campral®) in the fed state. Results are depicted in FIGS. 6 and 7 and the following Tables 16 and 17.

TABLE 16

Fed State and Fasting State Plasma Concentrations Following Oral Administration of 800 Mg of Sustained-Release Acamprosate Calcium Tablets to 12 Healthy Male Volunteers

| | Mean Plasma Concentration ng/mL | |
|---|---|---|
| Time (hr) | SR Acamprosate Ca 800 mg/ Fed | SR Acamprosate Ca 800 mg/ Fasted |
| 0 | 0 | 0 |
| 1 | 96 | 196 |
| 2 | 233 | 263 |
| 3 | 292 | 266 |
| 4 | 291 | 271 |
| 5 | 230 | 231 |
| 6 | 199 | 185 |
| 8 | 149 | 112 |
| 10 | 127 | 87 |
| 12 | 88 | 75 |
| 18 | 63 | 65 |
| 24 | 52 | 61 |
| 36 | 39 | 40 |
| 48 | 47 | 42 |

TABLE 17

Fed State and Fasting State Plasma Concentrations Following Oral Administration of 666 Mg of Enteric-Coated Acamprosate Calcium Tablets (Campral ®) to Six Healthy Male Volunteers

| | Mean Plasma Concentration (ng/mL) | |
|---|---|---|
| Time (hr) | Campral ® 666 mg/Fed | Campral ® 666 mg/fasted |
| 0 | 0 | 0 |
| 1 | 0 | 0 |
| 2 | 0 | 11 |
| 3 | 0 | 52 |
| 4 | 0 | 106 |
| 5 | 0.4 | 135 |
| 6 | 2 | 140 |
| 8 | 10 | 135 |
| 10 | 30 | 101 |
| 12 | 83 | 90 |
| 18 | 53 | 84 |
| 24 | 63 | 80 |
| 36 | 40 | 49 |
| 48 | 37 | 36 |

It is immediately evident that the pharmacokinetics of SR acamprosate calcium are very similar in the fed and fasting state; in fact they are bioequivalent according to FDA criteria. On the other hand the pharmacokinetics of Campral® are dramatically different in the fed and fasting state. In the data presented both $C_{max}$ and $AUC_{(0-48)}$ in the fed state are 41% lower than in the fasting state.

These pharmacokinetic data show that the SR acamprosate formulations of Example 3 are able to produce a mean acamprosate blood level greater than 200 ng/ml for more than four hours after a single 800 mg dose, whether it is given in either the fed or the fasting state. By contrast, assuming dose proportionality for Campral®, an 800 mg dose of Campral® would not attain this threshold in either the fed state or the fasting state. In fact, an 800 mg dose of Campral® in the fed state would produce a Cmax of only 100 ng/ml. A clear implication is that at equal milligram dosages SR acamprosate of EXAMPLE 3 will be more efficacious in treating neuropsychiatric disorders than Campral.

The formulations of the sustained release technology, including those of EXAMPLE 3, are grossly superior to Campral® in the fed state because they are much more bioavailable. In the fasting state the formulations have a $C_{max}$ 45% higher than the $C_{max}$ expected for an 800 mg dose of Campral®, based on the $C_{max}$ observed with the 666 mg dose and presuming dose proportionality. The higher $C_{max}$ implies a longer residence time at the threshold level necessary for therapeutic efficacy.

Given the large negative effect of administration with food on the bioavailability of Campral® tablets it is very surprising that there is no food effect at all on the bioavailability of the new formulations described herein. The observed bioequivalence of new formulations herein in the fed and fasting states implies that the adverse effect of food on the absorption of acamprosate in the intestines is exactly counterbalanced by the benefits for absorption of the sustained release of acamprosate into the stomach in the fed state. This equality of opposing effects is quite unusual and could not have been predicted from what is known about acamprosate and its previously known formulations.

Example 13

Four human volunteer groups were compared in this Phase 1 study: (A) 800 mg sustained release acamprosate tablets (in the fed state), (B) 800 mg sustained release acamprosate tablets (in the fasting state), (C) Campral® 666 mg (in the fasting state), and (D) acamprosate calcium 800 mg oral solution in water (in the fasting state). Plasma samples were collected within 1 hour (pre-dose) of dosing and 1, 2, 3, 4, 5, 6, 8, 10, 12, 18, 24, 36 and 48 hours after dosing.

And, acamprosate solution (or IR acamprosate tablets, because acamprosate is highly soluble in gastric or intestinal juices) will have a greater potential for side effects caused by a high local concentration of acamprosate or its associated cation in the GI tract. These facts together imply greater tolerability of SR acamprosate than IR acamprosate. (It is likely that Campral® was developed as an enteric-coated tablet because of concerns about GI side effects if an acamprosate tablet dissolved immediately in the stomach.). Furthermore, the bioavailability of IR acamprosate solution is reduced when it is taken in the fed state (REF), a problem not encountered with SR acamprosate. Thus, SR acamprosate is therapeutically superior to acamprosate solution in three ways: (1) It is more convenient to take a tablet than a liquid; (2) GI tolerability and possibly systemic toxicity are likely to be worse with the solution both because of a higher local concentration of the drug in the stomach and a higher plasma $C_{max}$ for a given residence time above a therapeutic threshold; and (3) SR acamprosate can be taken with food if desired without a loss of therapeutic effect, implying better treatment adherence and better GI tolerability, the latter because patients often tolerate medications if taken with food that cause GI upset if taken on an empty stomach. IR acamprosate tablets would be more convenient than acam-

TABLE 18

Summary (Mean and SD) of Pharmacokinetic Parameters for Acamprosate Plasma Pharmacokinetic Parameters in Healthy Subjects Administered Treatment A, B, C, and D

| Parameters | 800 mg sustained release Tablets, Fed | | 800 mg sustained release Tablets, Fasting | | Campral ® 666 mg Tablets, Fasting (dose normalized results) | | Acamprosate Calcium 800 mg solution, Fasting | |
|---|---|---|---|---|---|---|---|---|
| | N | Mean ± SD | N | Mean ± SD | N | Mean ± SD | N | Mean ± SD |
| $C_{max}$, ng/mL | 12 | 309 ± 108 | 12 | 322 ± 156 | 6 | 179 ± 106 | 6 | 528 ± 206 |
| $T_{max}$, h$^a$ | 12 | 3.00 [2.00, 4.00] | 12 | 2.00 [1.00, 4.00] | 6 | 8.00 [4.00, 12.00] | 6 | 1.00 [1.00, 2.00] |
| $AUC_{0-48}$, h · ng/mL | 12 | 3970 ± 841 | 12 | 3870 ± 1040 | 6 | 3400 ± 1050 | 6 | 5030 ± 576 |

: median [range];
NA; Not applicable;
Treatment A: 800 mg sustained release tablets (Synchroneuron Inc.) under fed conditions;
Treatment B: 800 mg sustained release tablets (Synchroneuron Inc.) under fasting conditions;
Treatment C: Campral ® 666 mg (two 333 mg tablets) (Forest Pharmaceuticals, Inc.) under fasting conditions;
Treatment D: Acamprosate calcium 800 mg oral solution in water (Synchroneuron Inc.) under fasting conditions.

The results:
(1) Confirm that SR acamprosate has equivalent AUC and $C_{max}$ in the fed and the fasting state;
(2) Show that the mean dose-normalized AUC of Campral® in the fasting state was 88% of the AUC of SR acamprosate in the fasting state, but the mean $C_{max}$ for Campral® was only 56% of the mean $C_{max}$ for SR acamprosate. Thus, the residence time of Campral® above a therapeutic threshold will be lower than that attained by SR acamprosate, and in some cases SR acamprosate will attain a therapeutic threshold blood level while Campral® at the same dose will not, even when the drug is taken in the fasting state.
(3) Show that acamprosate solution is more bioavailable than SR acamprosate in the fasting state, with AUC for the solution being 30% higher than the AUC for SR acamprosate. However, the $C_{max}$ for the solution was 64% higher. The disproportionately higher $C_{max}$ for the solution implies that the dose of solution needed to attain a given time above a therapeutic threshold will give a higher $C_{max}$ than the dose of SR acamprosate needed to attain the same therapeutic residence time. A higher Cmax implies a greater potential for adverse effects related to the plasma level of acamprosate.

prosate solution but would still be inferior to SR acamprosate.

Food Effects on Pharmacokinetics of 800 mg Sustained Release Tablets

The mean $C_{max}$ was 309 or 322 ng/mL, respectively, when 800 mg sustained release acamprosate formulation was dosed under fed and fasting conditions. The median $T_{max}$ in the fed group was one hour greater (3 hours vs. 2 hours) than that in the fasting group.

The rate and extent of absorption of 800 mg sustained-release acamprosate tablets, as reflected by peak exposure of $C_{max}$ and systemic exposure of $AUC_{0-t}$ values, were comparable (96.75% and 103.13%, respectively) between the test and reference treatments. The results indicate that there was no food effect on 800 mg sustained release acamprosate tablet in the rate and extent of absorption.

The 90% confidence interval for the geometric mean ratios of $C_{max}$ of acamprosate between the subjects taking SR acamprosate under the fed condition and the same subjects taking SR acamprosate in the fasting condition was [74.39%, 125.84%]. The 90% confidence interval for the geometric mean ratios of $AUC_{0-t}$ of acamprosate between the test treatment group (fed conditions) and the reference treatment group (fasting condition) was [88.74%, 119.85%].

TABLE 19

Statistical Comparisons of Acamprosate Plasma Pharmacokinetic Parameters in Healthy Male Volunteers Administered Single Oral Doses of 800 Mg Sustained Release Tablets under Fed and Fasting Conditions

| Drug | N | AUC (0-8 h) | AUC (0-12 h) | AUC (0-48) | Ratio of AUC (0-8) to AUC (0-48) | Ratio of AUC (0-12) to AUC (0-48) |
|---|---|---|---|---|---|---|
| SR Acamprosate - Fasted | 12 | 1621 | 1983 | 3872 | 0.416 | 0.512 |
| SR Acamprosate - Fed | 12 | 1593 | 2086 | 3967 | 0.400 | 0.525 |
| Campral - Fasting | 6 | 144.8 | 377.0 | 2168 | 0.0632 | 0.164 |
| Campral - Fed | 12 | 668 | 1098 | 3418 | 0.191 | 0.317 |

Note:
AUC(0-t) was calculated from the point PK data by linear interpolation. Means are arithmetic means. Mean ratio is the mean of the individual subjects' AUC ratios (not the ratio of the individual subjects mean AUCs.)
AUC Unit: ng*hr/mL Fasting State Statistical Comparison of 800 mg SR Acamprosate Tablets vs. Acamprosate Calcium 800 mg Oral Solution When healthy male volunteers received in the fasting state single oral doses of 800 mg acamprosate SR tablets and 800 mg acamprosate calcium solution the mean $C_{max}$ were 322 and 528 ng/mL, respectively. The median $T_{max}$ in the tablet group was one hour longer (2 hours vs. 1 hour) than that in the solution group.

The rate and extent of absorption of the test formulation (800 mg sustained release tablets) of acamprosate, as reflected by peak exposures $C_{max}$ and systemic exposures $AUC_{0-48}$ values, were slower (40.53%) and lower (24.81%) than those with the reference formulation (acamprosate calcium oral solution), respectively, under fasting conditions.

The 90% confidence intervals for the geometric mean ratios of the $C_{max}$ and the dose normalized $AUC_{0-48}$ of acamprosate between 800 mg sustained release acamprosate tablets acamprosate calcium oral solution) were ([41.57%, 85.09%]) and ([61.48%, 91.96%]), respectively.

The results indicate that under fasting conditions the relative bioavailability of the 800 mg SR acamprosate tablet compared to acamprosate calcium oral solution was 75.19%.

Fasting State Statistical Comparison of 800 mg Sustained Release Acamprosate Formulation vs. Campral® 666 mg When 800 mg sustained release acamprosate tablets and Campral® 666 mg were dosed under fasting conditions the mean dose-normalized $C_{max}$ were 322 and 179 ng/mL, respectively, when 800 mg sustained release acamprosate formulation and. The median $T_{max}$ in 800 mg sustained release formulation group was 6 hours shorter (2 vs. 8 hours) compared to that in Campral® 666 mg group.

The rate of absorption of the test formulation (800 mg sustained release tablet) of acamprosate, as reflected by peak exposures $C_{max}$ values, was faster (55.14%) compared to that of the reference formulation (Campral® 666 mg) under fasting conditions.

The extent of absorption of the test formulation (800 mg sustained release tablet) of acamprosate, as reflected by systemic exposures $AUC_{0-t}$ value, was comparable, 96.06%, to Campral® 666 mg under fasting conditions.

The 90% confidence intervals for the geometric mean ratios of the dose-normalized $C_{max}$ and the dose-normalized $AUC_{0-t}$ of acamprosate between the 800 mg sustained release formulation and Campral® 666 mg were [108.43%, 221.96%] and [78.55%, 117.48%], respectively, based on the statistical comparison results.

TABLE 20

Statistical Comparisons of Acamprosate Plasma Pharmacokinetic Parameters in Healthy Male Volunteers Administered Single Oral Doses of 800 Mg Sustained Release Tablets and Acamprosate Calcium 800 Mg Oral Solution under Fasting Conditions

| Treatment | N | GM (95% CI)[a] | | | |
|---|---|---|---|---|---|
| | | $C_{max}$* (ng/mL) | $AUC_{0-48}$* (hr · ng/mL) | $AUC_{0-\infty}$* (hr · ng/mL) | $T_{max}$** (hr) |
| 800 mg SR Tablets | 12 | 247 [190, 322] | 3134 [2670, 3679] | NA | 2.00 [1.00, 4.00] |
| Acamprosate Calcium Oral Solution | 6 | 416 [290, 597] | 4168 [3427, 5068] | NA | 1.00 [1.00, 2.00] |

| Comparison | GMR (in %)[90% CI] | |
|---|---|---|
| | $C_{max}$*** | $AUC_{0-48}$*** |
| SR Tablets vs. Acamprosate Calcium Oral Solution | 59.47 [41.57, 85.09] | 75.19 [61.48, 91.96] |

[a]GM = Geometric least-squares mean; CI = Confidence interval;
*Back-transformed least squares mean and confidence interval from mixed effects model performed on natural log-transformed values. $C_{max}$, $AUC_{0-48}$ and $AUC_{0-\infty}$ of acamprosate were normalized to 666 mg.
**Median (Minimum, Maximum).
***GMR = Geometric least-squares mean ratio between Treatments.
NA: Not available since $AUC_{0-\infty}$ could not be estimated for most subjects.

Thus, the results indicate that acamprosate is absorbed faster from the sustained release formulation, with the extent of absorption similar to Campral® 666 mg.

TABLE 21

Statistical Comparisons of Acamprosate Plasma Pharmacokinetic Parameters in Healthy Subjects Administered Single Oral Doses 800 Mg Sustained Release Tables and Campral ® 666 Mg Tablets Under Fasting Conditions

| Treatment | N | GM (95% CI)[a] | | | |
|---|---|---|---|---|---|
| | | $DNC_{max}$* (ng/mL) | $DNAUC_{0-48}$* (hr · ng/mL) | $DNAUC_{0-\infty}$* (hr · ng/mL) | $T_{max}$** (hr) |
| 800 mg sustained release Tablets | 12 | 247 [190, 322] | 3134 [2670, 3679] | NA | 2.00 [1.00, 4.00] |
| Campral ® 666 mg (2 × 333 mg) Tablets | 6 | 159 [111, 229] | 3262 [2682, 3967] | NA | 8.00 [4.00, 12.00] |

| Comparison | GMR (in %) [90% CI] | |
|---|---|---|
| | $C_{max}$*** | $AUC_{0-48}$*** |
| 800 mg sustained release tablets vs. Campral ® Tablets | 155.14 [108.43, 221.96] | 96.06 [78.55, 117.48] |

[a]GM = Geometric least-squares mean; CI = Confidence interval;
*Back-transformed least squares mean and confidence interval from mixed effects model performed on natural log-transformed values. $C_{max}$, $AUC_{0-48}$ and $AUC_{0-\infty}$ of acamprosate were normalized to 666 mg.
**Median (Minimum, Maximum).
***GMR = Geometric least-squares mean ratio between Treatments.
NA: Not available since $AUC_{0-\infty}$ could not be estimated for most subjects.
Treatment B: 800 mg sustained release tablets (Synchroneuron Inc.) under fasting conditions
Treatment D: Campral ® 666 mg (as two 333 mg tablets) (Forest Pharmaceuticals, Inc.) under fasting conditions Example 16

The highly unexpected finding of equivalent pharmacokinetics of the SR formulation in the fed and fasting states raised the question of whether the SR formulation tablet had the same fate in the fed and fasting states—whether, contrary to expectations, the tablet was retained in the stomach in the fasting state for several hours. Typically even large tablets are quickly ejected from the stomach by powerful "housekeeping waves" produced by intense periodic contractions of gastric muscles.

To answer the question a gamma scintigraphic study was undertaken using radiolabeled SR tablets according to EXAMPLE 3, which were taken by volunteer subjects in both the fed state and the fasting state. As will be seen, the study showed that the fate of the tablet differs greatly between the fed and fasting states; it is retained in the stomach for many hours in the fed state—4.5 hours in one of six subjects and over 16 hours in the remaining 5—and rapidly ejected into the small intestine in the fasted state. The study supports the following hypothesis for the mechanism underlying the fed-fasting pharmacokinetic equivalence of the sustained-release tablets: In the fed state, almost all of the acamprosate released by the SR tablet would be released in the stomach, and therefore the drug would be (would be exposed for potential absorption to the entire surface of the small intestine. By contrast, much of the acamprosate released by the tablet taken in the fasting state is released more distally in the small intestine—typically in the ileum. Relative to the SR tablet in the fasting state, the SR tablet in the fed state presents more of the acamprosate to the entire small intestine. Since the bulk of the absorption of acamprosate is by diffusion this increase in the area of intestinal surface to which the drug is exposed over time increases absorption in the fed state. In the fasting state relative to the fed state, the pill reaches the jejunum in less than 0.5 to 2.5 hours, before it has released even half of the drug. Differences between fed state and fasting state pharmacokinetics relate to the movement of the SR tablet through the GI tract, to a direct interference by food with absorption of the drug, and to the kinetics of release of the drug from the tablet. In the case of the SR tablets of EXAMPLE 3, we infer from in vitro studies that the rate of release of acamprosate from the tablet is the same in the fed state (where most of the drug is released into gastric juice approximate pH=1.0) and in the fasting state (where most of the drug is released into the jejunum and ileum at approximate pH=4.5). Remarkably the three factors that influence the PK of acamprosate from SNC-102 produce fed-fasting equivalence (of AUC and $C_{max}$). This truly remarkable, unexpected, and prospectively unpredictable finding was produced by the composition of matter described above utilizing a carbomer (Carbopol 974P) as the principal excipient, and it can be expected to be replicated by a sustained release tablet with somewhat different chemical composition, provided that: (1) The pill is sufficiently large (e.g., with at least one dimension exceeding 10 mm) that it will remain in the stomach for four hours or more if taken in the fed state; (2) The pill maintains its physical integrity in solution at either pH=1.0 or pH=4.5 for 12 hours or more; (3) The pill releases acamprosate in vitro with a similar time-concentration curve to the formulation described in EXAMPLE 3; and (4) the pill has essentially the same time-concentration curve at pH=1.0 and pH=4.5 For example, a pill utilizing Carbopol 971P as a principal excipient was shown to have these properties in vitro. Similar tablets utilizing these or other carbomers with various other secondary excipients have similar in vitro and in vivo properties, as sustained-release tablets made with various carbomer excipients have been shown to maintain their integrity in both highly acidic and less acidic solutions, and to release their active ingredient by diffusion.

Procedure of a Gamma Scintigraphy Study in Healthy Male Volunteers to Evaluate Gastric Retention of Samarium-153 Radiolabeled 800 mg Sustained-Release Acamprosate Tablets under Fasted and Fed Conditions The radionuclide used for this experiment was $^{153}$Sm with a gamma ray energy of 103 KeV and a half-life of 46 hours.

Non-radioactive $^{152}$Sm Samarium oxide in the amount of 3 milligrams was incorporated into each 800 mg SR acamprosate tablet. This was accomplished by manufacturing sustained-release acamprosate tablets containing 3 mg of a non-radioactive isotope of Samarium ($^{152}$Sm) and irradiating them at the MURR nuclear reactor (Columbia, Mo.) to create $^{153}$Sm. This was done according to directions supplied by Scintipharma.

The irradiation time was selected to yield about 70 microcuries of the $^{153}$Sm at the time of the scintigraphy experiment.

Subjects 001-006 were each administered dose forms at an appointed time which was designated as time zero (0.0).

Serial gamma scintigraphy images were acquired at 15 minute intervals over 10 hours elapsed time followed by an additional image acquisition at 12, 14 and 24 hours as needed to complete the study. Each 15 minute acquisition interval consisted of 3 one-minute data collections. The image collection times permitted the identification of the location of the radiolabeled dose form in the gastrointestinal tract at the respective time point to provide the time course for the passage of the tablet from one GI location to another.

For example, subject 001 in the fed condition retained the tablet in the stomach throughout the acquisition period of 16.5 hours, whereas the same subject, in the fasted state, emptied the tablet from the stomach at approximately 0.75 hours the duodenum, after which the tablet rapidly passed into the jejunum. The tablet remained in the jejunum until 2.75 hours when it moved into the ileum for about one hour, leaving at 4.5 hours into the ascending colon. After entering the transverse colon and residing there for 3 hours it moved into the descending colon where it was visible until 9.5 hours.

Figure 8:
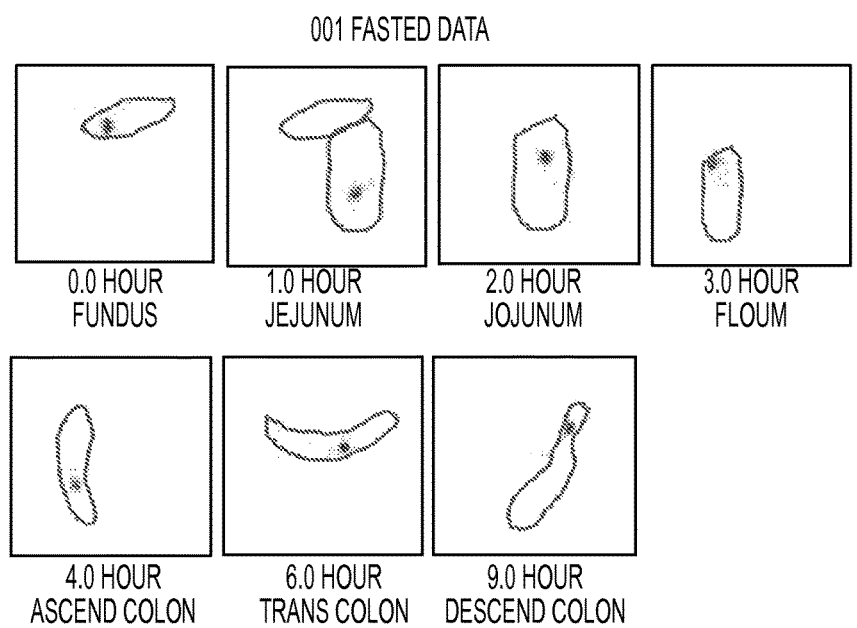
FIGS. 8 and 9 show gamma scintigraphy images of a tablet described herein in the GI tract of a subject who was administered the tablet in fasted and fed state.
Figure 9:
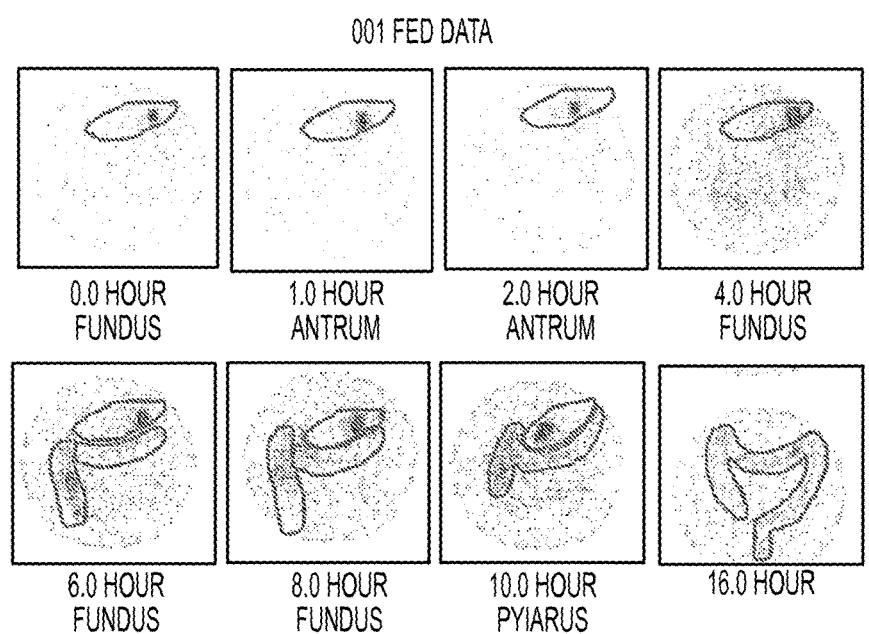
Figure 10:
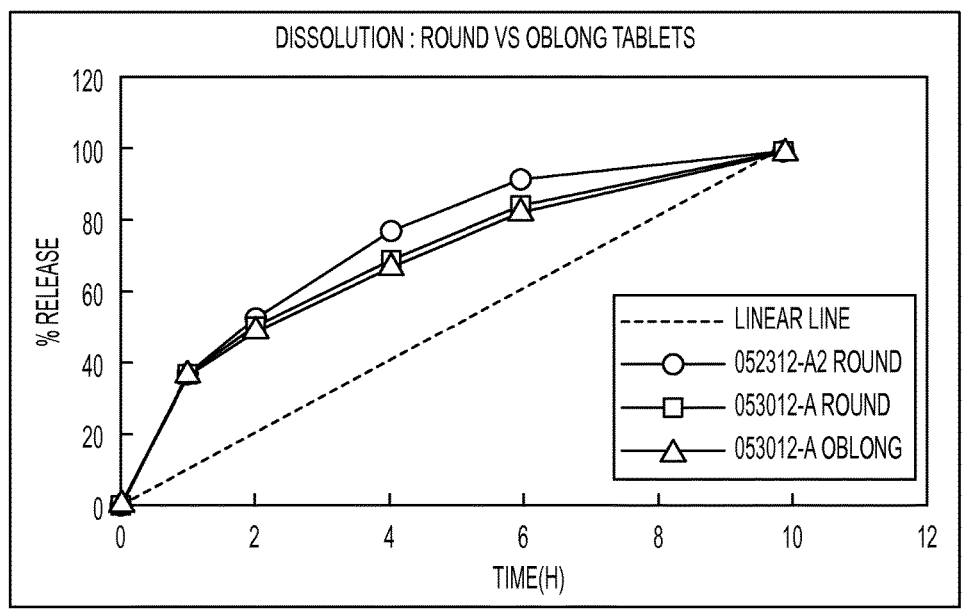

FIGS. 8 and 9 show the images of a tablet in the GI tract of subject 001. It can be seen that the tablet substantially retained its shape and dimensions in the GI tract in both fasted and fed states.

The GI tract residence time of subjects 001 to 006 is summarized in TABLE 22 below. The average retention times are shown in Table 23.

TABLE 22

Passage of 800 Mg SR Acamprosate Tablets Through The Gastrointestinal Tract of Healthy Male Volunteers in The Fed and Fasted States as Determined by Gamma Scintigraphy

| | | Residence Time (hours) for Each Subject | | | | | |
|---|---|---|---|---|---|---|---|
| | Location | 001 | 002 | 003 | 004 | 005 | 006 |
| Fed State | stomach | 16.5 | 16.5 | 16.5 | 16.5 | 4.5 | 16.5 |
| | jejunium | NA | NA | NA | NA | NA | NA |
| | ileum | NA | NA | NA | NA | 3 | NA |
| | ascending colon | NA | NA | NA | NA | 5.5 | NA |
| Fasted State | stomach | 0.75 | 0.25 | 2.25 | 2.25 | 0.75 | 0.25 |
| | jejunum | 2 | 1 | 1.25 | 2.25 | 1 | 1 |
| | ileum | 0.75 | 3.25 | 1 | 1 | 2.75 | 1 |
| | ascending colon | 1 | 1 | 3 | 9.5 | 8.5 | NA |
| | transverse colon | 3 | 1 | 1 | 1 | 11 | 1.25 |
| | descending colon | 1 | 1 | NA | NA | NA | 2 |

TABLE 23

Average Tablet Retention Time (hours) in Each GI Region

| GI Region | Fasted | Fed |
|---|---|---|
| Stomach | 1.1 | 14.4 |
| Jejunum | 1.4 | 0 |
| Ileum | 1.6 | 3 |
| Ascending Colon | 3.8 | 5.5 |
| Transverse Colon | 3 | 0 |
| Descending Colon | .7 | 0 |

The herein described subject matter sometimes illustrates different methods, compositions and/or components contained within, or combined with, different other methods, compositions and/or components. It is to be understood that the various described methods, compositions, components and combinations of the same are merely provided as non-limiting examples, and that in fact many others can be implemented which achieve the same purposes and/or functionality. Additional non-limiting examples polymers that can be utilized with the formulations and compositions described herein are found in PHARMACEUTICAL POLYMERS in MARTIN'S PHYSICAL PHARMACY AND PHARMACEUTICAL SCIENCES, Sixth Edition 2010, by Patrick J. Sinko and published by Wolters Kluwer, ISBN: 9780781797665, at Chapter 20, pp 492-515; electronically available via hypertext transfer protocol (http) at download-s.lww.com/wolterskluwer_vitalstream_com/sample-content/9780781797665_Sinko/samples/Chapter_20.pdf, which is incorporated herein by reference in its entirety.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the embodiments of the technology.

The publications discussed herein are provided solely for their disclosure prior to the filing date of the present application. Nothing herein is to be construed as an admission that the present embodiments are not entitled to antedate such publication by virtue of prior invention. Further, the dates of publication provided may be different from the actual publication dates, which may need to be independently confirmed. The subject matter disclosed in the publications, including any methods, compositions, excipients (including ranges and dosages of the same), etc., are incorporated herein by reference in their entireties.

Many modifications and variations of the embodiments described herein may be made without departing from the scope, as is apparent to those skilled in the art. Also, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising steps of:
   orally administering to a human subject in a fasted state a pill comprising about 20-95% by weight acamprosate, or a pharmaceutically acceptable salt thereof and about 1-30% by weight of a carbomer homopolymer type B.

2. The method of claim 1 wherein the carbomer homopolymer type B has a viscosity within a range of about 4,000 to about 39,400 cP.

3. The method of claim 1 wherein the pill is characterized in that it provides a Tmax of 1-4 hours to the subject in a fasted state.

4. A method comprising steps of:
   orally administering to a human subject in a fasted state an acamprosate pill comprising acamprosate in a dose within the range of 400 mg-1500 mg.

5. The method of claim 4 wherein the pill further comprises a polymer matrix that releases at least 36% of the acamprosate within 2 hours in vitro and at least 60% within 4 hours.

6. The method claim 4 wherein the pill is characterized in that it provides a Tmax of 1-4 hours to the subject in a fasted state.

7. The method of claim 4 wherein the acamprosate is in a pharmaceutically acceptable salt form.

8. The method of claim 7 wherein the pharmaceutically acceptable salt form is or comprises acamprosate calcium.

9. The method of claim 1, wherein the pill comprises about 1-6% by weight of a carbomer homopolymer type B.

* * * * *